United States Patent
Bharmi et al.

(10) Patent No.: US 9,610,444 B2
(45) Date of Patent: Apr. 4, 2017

(54) ERYTHROPOEITIN PRODUCTION BY ELECTRICAL STIMULATION

(71) Applicant: Pacesetter, Inc., Sunnyvale, CA (US)

(72) Inventors: Rupinder Bharmi, Canyon Country, CA (US); Stuart Rosenberg, Castaic, CA (US); Ryan Rooke, La Mesa, CA (US); Edward Karst, Los Angeles, CA (US); Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 363 days.

(21) Appl. No.: 14/218,740

(22) Filed: Mar. 18, 2014

(65) Prior Publication Data

US 2014/0288551 A1   Sep. 25, 2014

Related U.S. Application Data

(60) Provisional application No. 61/801,459, filed on Mar. 15, 2013.

(51) Int. Cl.
*A61N 1/36* (2006.01)
*A61B 18/14* (2006.01)
(Continued)

(52) U.S. Cl.
CPC ...... *A61N 1/36139* (2013.01); *A61B 5/14503* (2013.01); *A61B 5/486* (2013.01);
(Continued)

(58) Field of Classification Search
None
See application file for complete search history.

(56) References Cited

U.S. PATENT DOCUMENTS

| 3,731,681 A | 5/1973 | Blackshear et al. |
| 3,847,483 A | 11/1974 | Shaw et al. |

(Continued)

FOREIGN PATENT DOCUMENTS

WO   2004/062470   7/2004

OTHER PUBLICATIONS

American Heart Association, APS.720.04—Hypertension: Mechanisms of Vascular and Ventricular Decline, Presentation: 17 11 9—Renal Sympathetic Denervation Using an "Off-the-Shelf" Irrigated Radiofrequency Ablation, Catheter for the Management of Drug-Resistant Hypertension.

(Continued)

*Primary Examiner* — Kennedy Schaetzle
(74) *Attorney, Agent, or Firm* — Theresa A. Raymer

(57) ABSTRACT

Described herein are methods, devices, and systems for treating human anemia. The methods, devices, and systems generally include monitoring a patients hemoglobin level and at least one of autonomic balance and inflammatory state to determine the etiology of the anemic state, modulating at least one of a sympathetic or parasympathetic nerve based on the cause of the anemia, monitoring for changes in the patients cardiac activity and state of inflammation, and hemoglobin level. An external neurostimulation system is describes, and well as a chronic implantable system. A method for treating a patient for anemia in conjunction with a renal denervation ablation catheter is also disclosed.

11 Claims, 18 Drawing Sheets

(51) Int. Cl.
*A61B 5/145* (2006.01)
*A61B 18/00* (2006.01)
*A61B 5/00* (2006.01)
*A61B 5/0205* (2006.01)
*A61B 5/021* (2006.01)
*A61B 5/0215* (2006.01)
*A61B 5/20* (2006.01)

(52) U.S. Cl.
CPC ...... *A61B 18/1492* (2013.01); *A61N 1/36014* (2013.01); *A61N 1/36121* (2013.01); *A61B 5/021* (2013.01); *A61B 5/0205* (2013.01); *A61B 5/0215* (2013.01); *A61B 5/14535* (2013.01); *A61B 5/14542* (2013.01); *A61B 5/201* (2013.01); *A61B 5/4035* (2013.01); *A61B 2018/00404* (2013.01); *A61B 2018/00434* (2013.01); *A61B 2018/00511* (2013.01); *A61B 2018/00577* (2013.01)

(56) References Cited

U.S. PATENT DOCUMENTS

| | | |
|---|---|---|
| 3,951,147 A | 4/1976 | Tucker et al. |
| 4,114,604 A | 9/1978 | Shaw et al. |
| 4,692,147 A | 9/1987 | Duggan |
| 4,702,254 A | 10/1987 | Zabara |
| 4,712,555 A | 12/1987 | Thornander et al. |
| 4,772,263 A | 9/1988 | Dorman et al. |
| 4,788,980 A | 12/1988 | Mann et al. |
| 4,867,164 A | 9/1989 | Zabara |
| 4,940,052 A | 7/1990 | Mann et al. |
| 4,944,298 A | 7/1990 | Sholder |
| 5,025,807 A | 6/1991 | Zabara |
| 5,335,657 A | 8/1994 | Terry, Jr. et al. |
| 5,423,877 A | 6/1995 | Mackey |
| 5,466,254 A | 11/1995 | Helland |
| 5,476,483 A | 12/1995 | Bornzin et al. |
| 5,540,734 A | 7/1996 | Zabara |
| 5,578,061 A | 11/1996 | Stroetmann et al. |
| 5,840,069 A | 11/1998 | Robinson |
| 5,941,906 A | 8/1999 | Barreras et al. |
| 6,036,459 A | 3/2000 | Robinson |
| 6,176,242 B1 | 1/2001 | Rise |
| 6,292,695 B1 | 9/2001 | Webster, Jr. et al. |
| 6,314,323 B1 | 11/2001 | Ekwall |
| 6,409,675 B1 | 6/2002 | Turcott |
| 6,564,096 B2 | 5/2003 | Mest |
| 6,591,639 B2 | 7/2003 | Voth |
| 6,609,023 B1 | 8/2003 | Fischell et al. |
| 6,620,151 B2 | 9/2003 | Blischak et al. |
| 6,622,047 B2 | 9/2003 | Barrett et al. |
| 6,666,845 B2 | 12/2003 | Hooper et al. |
| 6,721,603 B2 | 4/2004 | Zabara et al. |
| 6,740,072 B2 | 5/2004 | Starkweather et al. |
| 6,845,267 B2 | 1/2005 | Harrison et al. |
| 6,937,896 B1 | 8/2005 | Kroll |
| 6,978,180 B2 | 12/2005 | Tadlock |
| 7,177,686 B1 | 2/2007 | Turcott |
| 7,313,442 B2 | 12/2007 | Velasco et al. |
| 7,344,717 B1 | 3/2008 | Swaak |
| 7,514,072 B1 | 4/2009 | Enrenreich et al. |
| 7,630,078 B1 | 12/2009 | Nabutovsky et al. |
| 7,634,315 B2 | 12/2009 | Cholette |
| 7,711,415 B1 | 5/2010 | Farazi et al. |
| 7,734,340 B2 | 6/2010 | De Ridder |
| 7,813,805 B1 | 10/2010 | Farazi |
| 7,869,869 B1 | 1/2011 | Farazi |
| 8,145,309 B2 | 3/2012 | Farazi et al. |
| 8,147,416 B2 | 4/2012 | Fayram et al. |
| 8,180,439 B2 | 5/2012 | Gill et al. |
| 8,192,360 B2 | 6/2012 | Koh et al. |
| 8,239,029 B2 | 8/2012 | De Ridder |
| 8,241,221 B2 | 8/2012 | Park |
| 8,326,429 B2 | 12/2012 | Wenzel et al. |
| 8,473,068 B2 | 6/2013 | Farazi |
| 8,478,403 B2 | 7/2013 | Wenzel et al. |
| 2003/0060857 A1 | 3/2003 | Perrson et al. |
| 2005/0075701 A1 | 4/2005 | Shafer |
| 2005/0075702 A1 | 4/2005 | Shafer |
| 2005/0149128 A1 | 7/2005 | Heil, Jr. et al. |
| 2005/0216062 A1 | 9/2005 | Herbst |
| 2006/0282131 A1 | 12/2006 | Caparso et al. |
| 2007/0239210 A1* | 10/2007 | Libbus ............... A61N 1/36114 607/2 |
| 2009/0062667 A1 | 3/2009 | Fayram et al. |
| 2010/0099964 A1 | 4/2010 | O'Reilly et al. |
| 2010/0114227 A1 | 5/2010 | Cholette |
| 2010/0152817 A1 | 6/2010 | Gillbe |
| 2010/0249865 A1* | 9/2010 | Zhang ................. A61B 5/0031 607/17 |
| 2011/0118726 A1 | 5/2011 | De La Rama et al. |
| 2011/0137298 A1 | 6/2011 | Nguyen et al. |
| 2012/0022612 A1 | 1/2012 | Littlewood et al. |
| 2012/0190991 A1 | 7/2012 | Bornzin et al. |
| 2012/0239104 A1 | 9/2012 | Rosenberg et al. |
| 2012/0290024 A1 | 11/2012 | Zhang et al. |
| 2012/0290053 A1 | 11/2012 | Zhang et al. |
| 2013/0085489 A1 | 4/2013 | Fain et al. |
| 2013/0090637 A1 | 4/2013 | Sliwa |
| 2013/0131753 A1 | 5/2013 | Simon |
| 2013/0184545 A1 | 7/2013 | Blomqvist et al. |
| 2013/0218029 A1 | 8/2013 | Cholette et al. |
| 2013/0245621 A1 | 9/2013 | Persson et al. |
| 2013/0282000 A1 | 10/2013 | Parsonage |
| 2013/0289650 A1 | 10/2013 | Karlsson et al. |

OTHER PUBLICATIONS

Anand, "Anemia and Chronic Heart Failure: Implications and Treatment Options," J. Am. Coll. Cardiol., 52: 501-511 (2008).
Bersin et al., "Importance of Oxygen-Haemoglobin Binding to Oxygen Transport in Congestive Heart Failure," Br Heart J., 70:443-447 (1993).
Bock et al., "Cardiorenal Syndrome: New Perspectives," Journal of the American Heart Association, 121:2583-2600 (2010).
Calbet, "Chronic Hypoxia Increases Blood Pressure eand Noradrenaline Spillover in Healthy Humans," J.Physiol, 55.1.1, 379-386 (2003).
Anemia as an independent prognostic factor for survival in patients with cancer: a systematic, quantitative review. Caro JJ, Salas M, Ward A, Goss G, Cancer. 2001;91:2214-2221.
Clause et al., "Stability of Oxyhemoglobin Affinity in Patients with Obstructive Sleep Apnea-Hypopnea Syndrome Without Daytime Hypoxemia," Journal of Applied Physiology, 105:1809-1812 (2008).
Das, "Can Vagus Nerve Stimulation Halt or Ameliorate Rheumatroid Arthritis and Lupus?", Lipids in Health and Disease, 10:19, 7 pages (2011).
Deng et al., "Splenorenal Reflex Regulation of Arterial Pressure," Hypertension, Journal of American Heart Association, 38:348-352 (2001).
DiBona et al., "Effect of Renal Denervation on Dynamic Authoregulation of Renal Blood Flow," Am J Physiol Renal Physiol, 286:F1209-F1218 (2004).
DiBona, "Dynamic Analysis of Patterns of Renal Sympathetic Nerve Activity: Implications of Renal Function," Exp Physiol, 90.2, 159-161 (2004).
DiBona et al., "Renal Hernodynamic Effects of Activation of Specific Renal Sympathetic Nerve Fiber Groups," The American Physiological Society, R539-R649 (1999).
Du et al., "Response to cardiac sympathetic activation in transgenic mice overexpressing beta 2-adrenergic receptor", Am J Physiol Heart Circ Physiol, 271: H630-H636 (1996).
Flanagan et al., "In Vivo Imaging of Hepcidin Promoter Stimulation by Iron and Inflammation," Blood Cells Mol Dis, 38(3): 253-257 (2007).
Gaber et al., "Hypoxia Inducible Factor (HIF) in Rheumatology: Low O2! See what HIF Can Do!," Annals of the Rheumatic Diseases, 64:971-980 (2005).

(56) References Cited

OTHER PUBLICATIONS

Gebhard et al., "Role of Renal Nerves and Salt Intake on Erythropoietin Secretion in Rats Following Carbon Monoxide Exposure," The Journal of Pharmacology and Experimental Therapeutics, 319(1) 2006.
Giaccia et al., "The Biology of Hypoxia: The Role of Oxygen Sensing in Development, Normal Function, and Disease," Genes & Development, 18: 2183-2194 (2004).
Aarpo, Matti; "An Updated on Twenty Years of Anemia Management with Erythropoiesis-Stimulating Agents in Nephrology and Oncology/Hematogology," The Oncologist, 14(suppl 1): 1-5 (2005).
Grassi et al., "How to Assess Sympathetic Activity in Humans," Journal of Hypertension, 17:719-734 (1999).
Grentz, et al., "Lack of Effect of Extracellular Adenosine Generation and Signaling on Renal Erythropoietin Secretion During Hypoxia," Am J Physiol Renal Physiol, 293: F1501-F1511 (2007).
Gunaratnam et al., "HIF in Kidney Disease and Development," J Am Soc Nephrol, 20: 1877-1887 (2009).
Gupta et al., "Clinical Benefits of Two Different Schedules of Recombinant Human Erythropoietin in Anemic Patients with Advanced Head and Neck Cancer," BioScience Trends, 4(5): 267-272 (2010).
Halperin et al., "Properties Permitting in the Renal Cortex to be the Oxygen Sensor for the Release of Erythropoietin: Clinical Implications," Clin J Am Soc Nephrol, 1:1049-1053 (2006).
Hamza et al., "Splenorenal Reflex Modulates Renal Blood Flow in the Rat," Am J. Physiol. 558(1):277-282 (2004).
Hamza et al., "Effect of Mesenteric Vascular Congestion on Reflex Control of Renal Blood Flow," Am J. Physiol Regul Comp Physiol, 293:R1917-R1922 (2007).
D. Hering, Renal Denervation in Moderate to Severe CKD, JASN ASN.2011111062 (2012).
Hertig et al., "Correction of Anaemia on Dialysis: Did We Forget Physiology!", Nephrol Dial Transplant, 36: 1120-1122 (2011).
Jazrawi et al., "Erythropoietin Levels in Cardiac Resynchronization Therapy Responders," International Journal of Cardiology, 2 pages (2009).
Kawashima, "The autonomic nervous system of the human heart with special reference to its origin, course, and peripheral distribution", Anat Embryol. (2005) 209: 425-438.
Kingwell et al., "Assessment of Gain Tachycardia and Bradycardia Responses of Cardiac Baroreflex," Am J. Physiol Heart Circ Physiol, 260:H1254-H1263 (1991).
Komajda, "Anemia in Chronic Heart Failure," Journal of the American College of Cardiology. 49(7): 763-764 (2007).
Koplan et al., "Renal Interactions of Renin-Angiotensin System, Nitric Oxide and Superoxide Anion: Implications in the Pathophysiology of Salt-Sensitivity and Hypertension," Physiol. Res. 58 (Suppl. 2) S55-S67, 2009.
Kupnik et al., "Erythropoietin in Post-Resuscitation Neurological Recovery: Is There Light at the End of the Tunnel?", SIGNA VITAE, 2(1): 11-14 (2007).
Lee et al., "Prevention of Erythropoietin—Associated Hypertension," Hypertension, (2010).
Leonard et al., "Differential Regulation of the Oscillations in Sympathetic Nerve Activity and Renal Blood Flow Following Volume Expansion," 83: 19-18 (2000).
Marsden, "Erythropoietin—Measurement and Clinical Applications," The Association for Clinical Biochemistry, 43:97-104 (2006).
Melivier et al., "Pathophysiology of anaemia: focus on the heart and blood vessels," Nephrology Dial Transplant, 15 [Suppl 3]: 14-18 (2000).
Mizeres, "The cardiac plexus in man", Am. J. Anat. 112:141-151 (1963).
Moncrief et al., "Splenic Baroreceptors Control Splenic Afferent Nerve Activity," Am J Physiol Regul Integr Comp Physicol, 209:R352-R356 (2006).
Murakami et al., "Effects of cardiac sympathetic nerve stimulation on the left ventricular end-systolic pressure-volume relationship and plasma norepinephrine dynamics in dogs", Jpn. Circ. J. 61(10): 864-71 (1997).
Oberhoff et al. (1998) Ann Oncol 9:255-260.)
Oliver et al., "Regulation of NFkB Signalling During Inflammation: The Role of Hydroxylases." Arthritis Research & Therapy, 11:215, pp. 1-8 (2009).
Parsi et al., "Anaemia in Heart Failure: Its Diagnosis and Management," The European Journal of Heart Failure, 5: 3-4 (2003).
Pauza et al., "Morphology, distribution, and variability of the epicardiac neural ganglionated subplexuses in the human heart", The Anatomical Record 259(4): 353-382 (2000).
Reider, Dr. W. "Successful test, uremic conditions to be treated surgically." Archive for Clinical Surgery, Julius Springer Publishers (1935) (translation from German).
Rogers et al., "Hypoxia Limits Antioxidant Capacity in Red Blood Cells by Altering Glycolytic Pathway Dominance," The FASEB Journal, 23: 3159-3170 (2009).
Roy P., et al., "Recent Trends in the Nitrergic Nervous System," Indian Journal of Pharmacology, 37(2): 69-76 (2005).
Ruifrok et al., "Heart Failure-Associated Anemai: Bone Marrow Dysfunction and Response to Erythropoietin," J Mol Med. 89:377-387 (2011).
Sangkatumvong et al., "Abnormal Autonomic Cardiac Response to Transient Hypoxia in Sickle Cell Anemia," Physiological Measurement, 29: 655-668 (2008).
Semenza, Involvement of Oxygen-Sensing Pathways in Physiologic and Pathologic Erythropoiesis, Blood Journal, 114: 2015-2019 (2009).
Sharkey et al., "Acute Effects of Hypoxaemia, Hyperoxaemia and Hypercapnia on Renal Blood Flow in Normal and Renal Transplant Subjects," Eur. Respir J, 12: 653-657 (1998).
Shloi et al., "Rapamycin Attenuates Load-Induced Cardiac Hypertrophy in Mice", Circulation 2003; 107:1664.
Shin et al., "Assessment of autonomic regulation of heart rate variability by the method of complex demodulation," IEEE Transactions on Biomedical Engineering, vol. 36, No. 2, Feb. 1989.
G. Simonetti, et al., Endovascular Radiofrequency Renal Denervation in Treating Refractory Arterial Hypertension: a Preliminary Experience, Rediol Med, 117(3):426-44. (Apr. 2012).
Solomon et al., "Erythropoietic Response and Outcomes in Kidney Disease and Type 2 Diabetes." The New England Journal of Medicine, 1146-111155, (2010).
Suehiro, et al., "Selective Renal Vasodilation and Active Renal Artery Perfusion Improve Renal Function in Dogs with Acute Heart Failure," The Journal of Pharmacology and Experimental Therapeutics, 298(2):1154-1160 (2001).
Tang et al., "Effects of Recombinant Human Erythropoietin on Platelet Activation in Acute Myocardial Infarction: Results of a Double-Blind, Placebo-Controlled, Randomized Trial," 158(6): 941-947.
Teixeira, M. C. B. et al. "Role of the peripheral renin profile in predicting blood pressure control after bilateral nephrectorny in renal-transplanted patients." Nephrol Dial Transplant, 13:2092-2097 (1998).
G. Thomas, et al., Renal denervation to treat resistant hypertension: Guarded optimism, Cleveland Clinic Journal of Medicine, 79(7):501-510 (2012).
G. Thomas et al., "Neural Control of the Circulation," Adv Physiol Edu, 35: 28-32 (2011).
Toda et al., "Gastrointestinal Function Regulation by Nitrergic Efferent Nerves." Pharamacological Reviews, 57(3):315-335 (2005).
Safety and efficacy of a novel multi-electrode renal denervation catheter in resistant hypertension: 3 month data from the EnligHTN I trial, Worthley S., Tsioufis C., Worthley M., Sinhal A., Chew D., Meredith I., Malaiapan Y., Papademetriou V., Journal of the American College of Cardiology 2012 60 SUPPL. 17 (B62).
Tulppo M P et al. Physiological background of the loss of fractal heart rate dynamics. Circulation, Jul. 19; 112 (3):314-9, 2005.
U.S. Appl. No. 60/591,195 entitled "Stimulation System and Method for Treating a Neurological Disorder".

(56) References Cited

OTHER PUBLICATIONS

U.S. Appl. No. 11/283,229, filed Nov. 18, 2005, entitled "Endovascular Lead System for Chronic Nerve Stimulation".
U.S. Appl. No. 10/972,278, entitled "Implantable Device With Responsive Vascular and Cardiac Controllers".
Valente, in Laparoscopic Renal Denervation for Intractable ADPK-Related Pain, Nephrol Dial Transplant 16:60 (2001).
Van Der Meer et al., "Adequacy of Endogenous Erythropoietin Levels and Mortality in Anaemic Heart Failure Patients," European Heart Journal, 29:1510-1515 (2008).
Veelken et al., "Autonomic Renal Denervation Amerlicrates Experimental Glomerulonephritis," J. Am. /soc Nephrol, 19:1371-1378 (2008).
Ventura el al., "Nitrergic Modulation of Vasopressin, Oxytocin and Atrial Natriuretic Peptide Secretion in Response to Sodium Intake and Hypertonic Blood Volume Expansion," Braz J Med Bio Res, 35(9): 1101-1109 (2002).
Vida et al., "$\alpha 7$-Cholinergic Receptor Mediates Vagal Induction of Splenic Norepinephrine," The Journal of Immunology, 7 pages (2011).
Wallin et al., "Renal Noradrenaline Spillover Correlates with Muscle Sympathetic Activity in Humans," Journal of Physiology, 491(3): 881-887 (1996).
Wenger et al., "Regulated Oxygen Sensing by Protein Hydoxylation in Renal Erythropoietin-Producing Cells," Am J. Physiol Renal Phsyiol, 298:F1287-F1296 (2010).
Westenbrink et al., "Anaemia in Chronic Heart Failure is Not Only Related to Impaired Renal Perfusion and Blunted Erythropcietin Production, but to Fluid Retention as Well," European Heart Journal, 28, 166-171 (2007).
Zazgornik, J., "Bilateral Nephrectomy: The best, but often overlooked, treatment for refractory hypertension in hemodialysis patients." Am J. Hypertenson 11:1364-1370 (1998).

\* cited by examiner

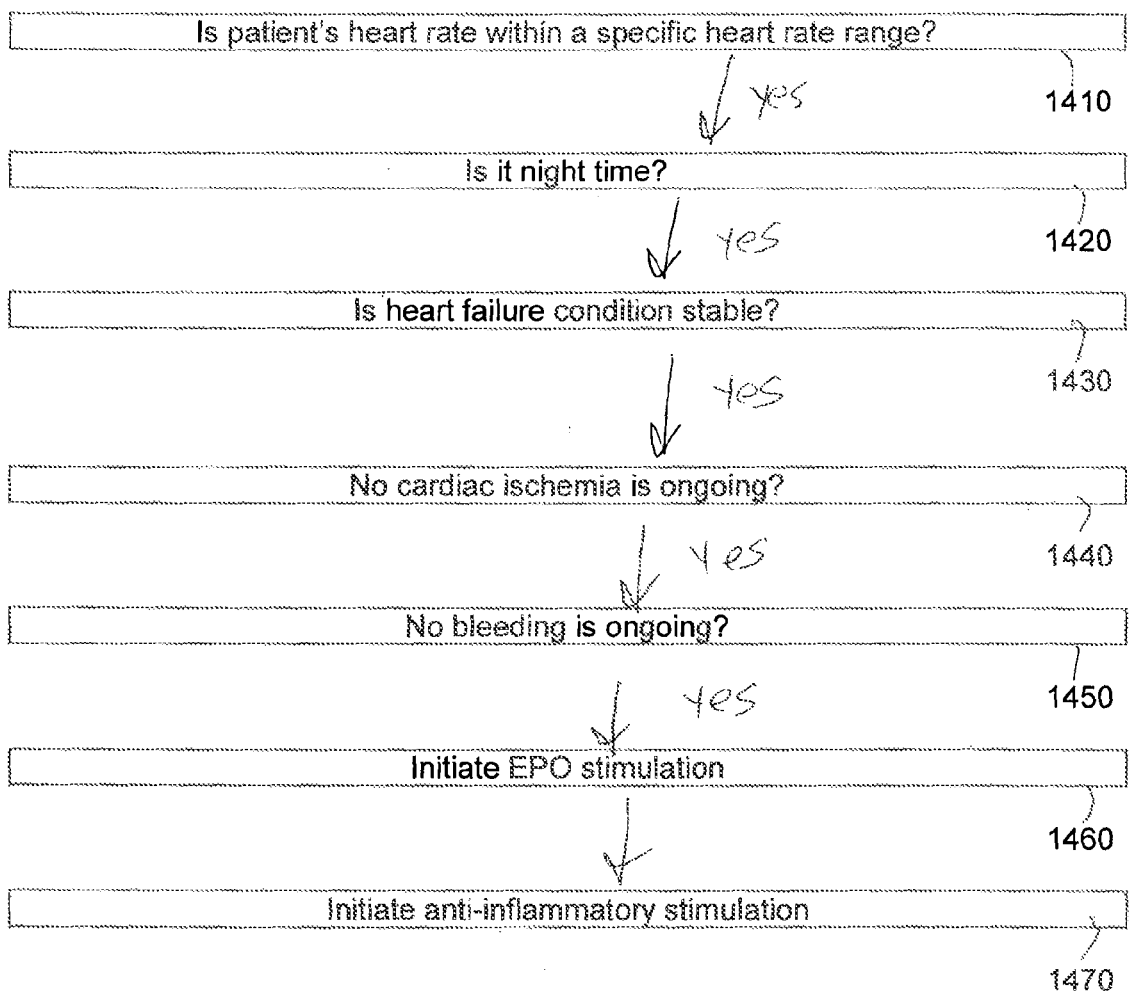

FIG. 13

```
stimulation device 100 monitors the hemoglobin levels of the patient on a
continual (e.g., periodic) basis
1305
                              ↓
stimulation device 100 monitors at least one of autonomic balance or
inflammatory state of the patient on a continual (e.g., periodic) basis
1310
                              ↓
determining an anemic condition based on the hemoglobin level and at least one
of the autonomic balance or inflammatory state
1315
                              ↓
anemia monitor 240 selects electrical stimulation parameters based on one or
more characteristics of the indicated anemic condition
1320
                              ↓
anemia monitor 240 determines whether to provide stimulation of
parasympathetic innervation, sympathetic innervation, or a combination of the
two
1325
                              ↓
generate one or more stimulation signals to stimulate the patient's nervous
system
1330
                              ↓
monitor cardiac activity, e.g., IEGM data and/or impedance data, to determine
the effect of the stimulation on the patient's condition and adapt the stimulation
accordingly
1335
                              ↓
modify stimulation parameters if the severity of the anemic condition has
changed, if the patient's heart rate has changed, if there has been a change in
the quantity or severity of observed PVCs, if there has been a change in cardiac
integrity
1340
                              ↓
terminate stimulation if anemia is no longer indicated
1320
```

```
┌─────────────────────────────────────────────────────────────────┐
│ radiofrequency catheter ablation device is used to ablate the   │
│ renal nerves of a patient                                       │
│                          1510                                   │
└─────────────────────────────────────────────────────────────────┘
          │                    │                         │
          ▼                    ▼                         ▼
┌──────────────────┐  ┌──────────────────┐  ┌──────────────────────┐
│ Replace lead     │  │ Permanently      │  │ Use central          │
│ with             │  │ implant modified │  │ nervous system       │
│ permanently      │  │ RF catheter      │  │ neuromodulation      │
│ implantable lead │  │ ablation device  │  │ and/or stimulate     │
│ 1520             │  │ so that tip of   │  │ the production of    │
│                  │  │ lead is secured  │  │ catecholamines       │
│                  │  │ distal to tip of │  │ and                  │
│                  │  │ ablation site in │  │ neuropeptides        │
│                  │  │ order to provide │  │ and/or vagal         │
│                  │  │ for              │  │ nerve                │
│                  │  │ neurostimulation │  │ stimulation          │
│                  │  │ 1530             │  │ 1540                 │
└──────────────────┘  └──────────────────┘  └──────────────────────┘
```

FIG. 15

ERYTHROPOEITIN PRODUCTION BY ELECTRICAL STIMULATION

PRIORITY CLAIM

This application claims the benefit of U.S. Provisional Application No. 61/801,459, filed Mar. 15, 2013 and is incorporated herein by reference in its entirety to provide continuity of disclosure.

TECHNICAL FIELD

This application relates generally to implantable stimulation devices and, more specifically, but not exclusively to providing electrical stimulation to increase the production of erythropoietin.

BACKGROUND

Anemia is defined by the World Health Organization's as hemoglobin concentration <13.0 g/dl in men and <12.0 g/dl in women. Approximately nine percent of the general adult population meets this definition of anemia. The prevalence of anemia ranges from less than 10% among patients with mild heart failure to more than 50% for those with advanced disease.

Anemia has been shown to be a powerful predictor of rehospitalization rates and survival in chronic heart failure. Most studies have shown a linear relationship between hematocrit or hemoglobin and survival with the SOLVD (Studies of Left Ventricular Dysfunction) trial reporting a 2.7% increase in the adjusted risk of death per 1% reduction in hematocrit and the PRAISE (Prospective Randomized Amlodipine Survival Evaluation) trial describing a 3% increase in risk for each 1% decline in hematocrit. The significance of anemia among patients hospitalized with acute decompensated heart failure has been examined. Felker et al. retrospectively analyzed the OPTIME-CHF (Outcomes of a Prospective Trial of Intravenous Milrinone for Exacerbations of Chronic Heart Failure) results and found that hemoglobin level independently predicted adverse events, even after adjustment for other covariates. For every 1 g/dl decrease in admission hemoglobin value, a 12% increase in the probability of death or rehospitalization within 60 days of treatment was observed. Recently, the same investigators studied anemia in patients with heart failure and preserved systolic function. Anemia was once again found to be independently associated with adverse outcomes (adjusted hazard ratio: 1.6 to 1).

Chemotherapy-induced anemia (CIA) is a frequent complication in cancer patients receiving conventional myelosuppressive chemotherapy. Anemia affects up to 90% of cancer patients. The relative risk of death in patients with cancer has been determined to increase by 65% in the presence of anemia. *Anemia as an independent prognostic factor for survival in patients with cancer: a systematic, quantitative review.* Caro J J, Salas M, Ward A, Goss G, Cancer, 2001; 91:2214-2221.

In the case of Hodgkin's lymphoma, a cancer that is currently curable in approximately two thirds of patients, a hemoglobin level of less than 10.5 g/dl at the time of diagnosis is one of seven risk factors. The hemoglobin level is the strongest of three risk factors at relapse. There is a statistically significant difference in overall survival time between females having a hemoglobin level of less than 10.5 g/dl and females having a hemoglobin level of greater than 10.5 g/dl. There is also a statistically significant difference in overall survival time between males having a hemoglobin level of less than 12 g/dl and males having a hemoglobin level of greater than 12 g/dl.

The glycoprotein hormone erythropoietin (EPO) is the principal factor responsible for the regulation of red blood cell production. EPO acts in concert with other factors to stimulate the proliferation and maturation of responsive bone marrow erythroid precursors. EPO affects expansion of progenitor cells by repressing apoptosis (programmed cell death) and by acting as a mitogen to increase production. EPO, along with other factors, also decreases the maturation time of red blood cells in the bone marrow.

Erythropoeitic agents have been shown to reduce the need for blood transfusions and their associated complications in cancer patients undergoing chemotherapy, as demonstrated by several clinical trials. Daily subcutaneous administration of EPO stimulation therapy administration at a dose of 5000 IU increases hemoglobin levels and reduces transfusion requirements in chemotherapy-induced anemia, especially during platinum-based chemotherapy. (Oberhoff et al. (1998) Ann Oncol 9:255-260.) However, it is estimated that 30% to 50% of patients undergoing chemotherapy and receiving EPO stimulation therapy treatment are hyporesponsive or refractory to the recombinant EPO therapy. (J. Glaspy (2005) Expert Opin. Emerging Drugs 10:553-567.) In addition, synthetic EPO is known to have serious issues. Blood transfusions are also associated with negative consequences, such as iron overload which can cause cancer and/or death due to end-stage organ failure.

EPO is produced primarily in the kidney by endothelium of peritubular capillaries in the renal cortex. Additionally, the liver, macrophages in the bone marrow, and astrocytes in the central nervous system (CNS) make small amounts of EPO.

Various techniques are described herein for providing electrical stimulation to increase the production and efficacy of erythropoietin. Such techniques are optionally implemented, for example, in patients suffering from anemia from a variety of etiologies.

SUMMARY

A summary of several sample aspects of the disclosure follows. It should be appreciated that this summary is provided for the convenience of the reader and does not wholly define the breadth of the disclosure. For convenience, one or more aspects or embodiments of the disclosure may be referred to herein simply as "some aspects" or "certain embodiments."

The disclosure relates in some aspects to electrical stimulation for increasing erythropoietin production.

The disclosure relates in some aspects to stimulation of the intrinsic nervous system at the heart in order to restore a healthy balance of the sympathetic nervous system in order to treat anemia.

The disclosure relates in some aspects to renal nerve stimulation for increasing erythropoietin production.

The disclosure relates in some aspects to spinal cord stimulation for increasing red blood cell production.

The disclosure relates in some aspects to deep brain stimulation for increasing erythropoietin production. In certain embodiments, the hypothalamus is stimulated to increase erythropoietin production. In certain embodiments, the medulla oblongata is stimulated to increase erythropoietin production. In certain embodiments, the hypothalamus in blocked in order to decrease inflammation.

The disclosure relates in some aspects to carotid sinus nerve (CSN) stimulation for increasing erythropoietin production.

The disclosure relates in some aspects to cervical nerve stimulation for increasing erythropoietin production.

The disclosure relates in some aspects to chemical stimulation of the kidneys to produce EPO.

The disclosure relates in some aspects to stimulation of sympathetic ganglion of the parathyroid gland for increasing erythropoietin production.

The disclosure relates in some aspects to vagus nerve stimulation for increasing red blood cell production and inhibition of the production of inflammatory cytokines.

In certain embodiments, the system may be a closed-loop system that continuously monitors for quality and quantity of blood production for oversight.

In certain embodiments, the system includes multiple sensors that may determine EPO, nitrogen oxide, hemoglobin, hematocrit, hepcidin, iron, ferritin, transferrin, serum albumin, Vitamin B12, folate, 25-hydroxyvitamin D, phosphate, oxygen, carbon dioxide, creatinine, blood urea nitrogen, compound activation potential of a nerve, anti-inflammatory cytokine concentrations, pro-inflammatory cytokine concentrations, heat shock protein (HSPs) levels (indicative of inflammation), blood pressure, pH, and/or impedance, which may be used to determine the cause of anemia, an appropriate therapeutic strategy, to continuously monitor for quality and quantity of blood production and the effect of changes on EPO, and to adjust the system's parameters in a closed-loop.

In certain embodiments, the system adjusts the neuromodulation based on the monitored cardiac integrity, inflammation markers, EPO concentration, hemoglobin concentration, blood pressure and/or blood volume of the patient.

Adjusting the neuromodulation comprises modifying at least one of a plurality of electric activation parameters including a current level, a pulse width, a frequency, a duty cycle, and a location of the patient's body to which the electric activation is applied.

Adjusting the electric activation may comprise referring to a lookup table which provides electric activation plans for different conditions of monitored sympathetic balance, EPO, inflammation marker, blood pressure, and blood volume, the electric activation plans each specifying a setting of at least one of a plurality of electric activation parameters including a current level, a pulse width, a frequency, a duty cycle, and a location of the patient's body to which the electric activation is applied.

In certain embodiments, the renal nerves are ablated prior to neurostimulation.

The disclosure relates in some aspects to an exterior neurostimulator that can be used to treat anemia.

The disclosure relates in some aspects to an implantable neurostimulator that can be used to treat anemia.

The disclosure relates in some aspects to determining whether a patient is having an acute episode of heart failure prior to initiating neurostimulation to treat anemia.

The disclosure relates in some aspects to methods of determining inflammation using a nerve's compound action potential.

The disclosure relates in some aspects to methods of determining inflammation specifically caused by EPO stimulation.

These and other features and advantages of the present invention will become apparent to those of ordinary skill in the art in view of the following detailed description of the specific embodiments.

BRIEF DESCRIPTION OF THE DRAWINGS

These and other features, aspects, and advantages will be more fully understood when considered with respect to the following detailed description, the appended claims, and the accompanying drawings, wherein:

FIG. 12 is a simplified flowchart of an embodiment for triggering the initiation of neurostimulation therapy for treatment of anemia according to certain embodiments;

FIG. 13 is a simplified flowchart of an embodiment providing a treatment method according to certain embodiments;

FIG. 15 illustrates an example method according to certain embodiments;

Figure 1:
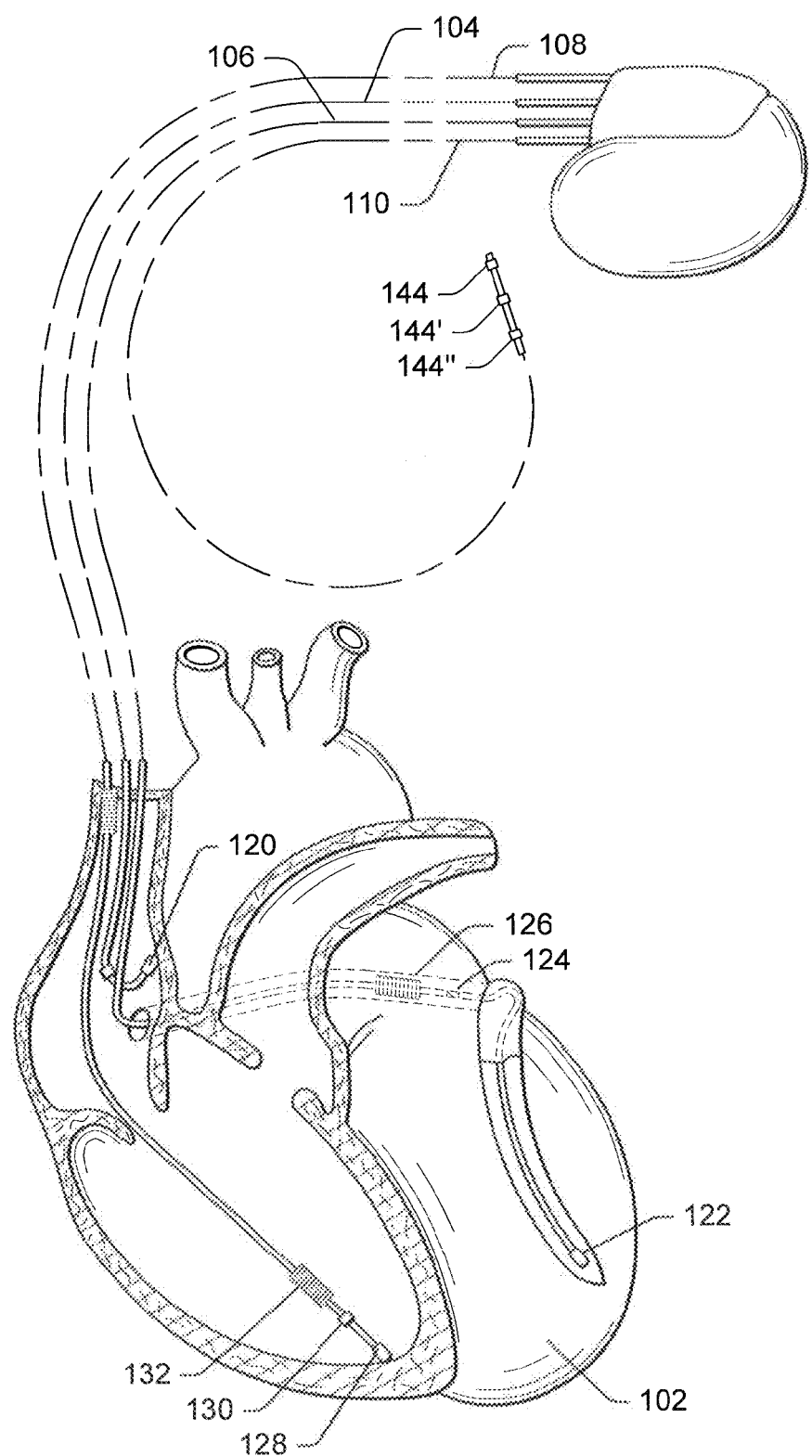
FIG. 1 is a simplified diagram of a stimulation device implanted in a patient according to certain embodiments.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Overview

Production of EPO

Erythropoietin (EPO) is produced by peritubular fibroblasts of the renal cortex of the kidney in response to local oxygen tension (renal interstitial $PO_2$). $PO_2$ in the renal cortex is proportional to the ratio of glomerular filtration rate (GFR) ($O_2$ consumption) to renal blood flow (RBF) ($O_2$ delivery). The higher the ratio of GFR to RBF (the filtration fraction), the more $O_2$ extracted per liter of blood flow in the renal cortex. Reduced oxygen tension in the peritubular fibroblasts of the renal cortex is associated with increased intracellular concentrations of reactive oxygen species, which, in turn, increases activation of hypoxia inducible factor-1 (HIF-1) and erythropoietin gene expression.

Under hypoxic conditions, the production of EPO begins within minutes to hours and reaches a maximum production within 24 hours. Hypoxia generates a detectable increase in serum EPO within 90 minutes. New red blood cells may not appear until about 5 days later. When large quantities of EPO are formed and there is sufficient iron and required nutrients (e.g., folic acid, vitamin B12, and vitamin D), the rate of red blood cell production can increase over ten fold.

The production of EPO is controlled at the transcriptional level. The hypoxia-inducible transcription factors (HIFs) are inactivated in normoxia by enzymatic hydroxylation of their α-subunits. Hypoxia attenuates the inhibition of the EPO promoter by GATA-2 and promotes the availability of heterodimeric (α/β) HIFs (predominantly HIF-2) which stimulate the EPO enhancer. Levels of the HIF-1α subunit increase exponentially as $O_2$ concentration declines. Three HIF-α prolyl hydroxylases (PHD-1, -2 and -3) initiate proteasomal degradation of HIF-α, while an asparaginyl hydroxylase ("factor inhibiting HIF", FIH-1) inhibits the transactivation potential. The HIF-α hydroxylases contain $Fe^{2+}$ and require 2-oxoglutarate and ascorbate as co-factors. HIF is rapidly degraded upon reoxygenation. In the presence of oxygen, there is a hydroxylation of a proline residue within a highly conserved region in the oxygen-dependent degradation domain of HIF-1α. This structural modification of HIF-1α enables it to bind to von Hippel-Lindau protein, an interaction necessary for the ubiquitination of HIF-1α and its degradation within the proteasome.

EPO binds to EPO receptors (EPOR) on erythroid progenitor cells (burst forming units-erythroid (BFU-E) and colony-forming-unit-erythroid (CFU-E)) in the bone marrow to initiate erythropoiesis. During erythropoiesis large amounts of iron are used by the bone marrow to synthesize hemoglobin. In the liver, HIF-1 stimulates the absorption and delivery of iron to the bone marrow by repressing the gene encoding hepcidin, an inhibitor of ferroportin, the main protein responsible for intestinal iron uptake. HIF-1 also activates hepatic synthesis of transferrin, the main plasma protein responsible for transporting iron from the intestine to the bone marrow via the transferrin receptor.

In non-neuronal cells, binding of EPO triggers dimerization of EPO receptors resulting in JAK2 activation. Three different signal transduction pathways are predominantly activated thereafter: the RAS/RAF/ERK (ERK1/2) pathway; the PI3K/Akt pathway; and the Signal Transducer and Activator of Transcription 5 (STAT5), which upon phosphorilation by JAK2 translocates to the nucleus and initiates transcription of anti-apoptotic genes, including Bcl-XI.

The Inflammatory Response to Hypoxia

EPO has been shown to have a bell-shaped dose response curve both in vitro and in vivo. While too little EPO may be ineffective, EPO overproduction initiates a pro-inflammatory response by, e.g., stimulating the production of pro-inflammatory cytokines, which suppress the effectiveness of the EPO. Sustained hypoxia leads to the activation of nuclear factor κB (NF-κB). NF-κB plays a central role in the inflammatory response with an increased production of pro-inflammatory cytokines including tumour necrosis factor α (TNF-α), interleukin 6 (IL-6), interleukin 8 (IL-8), and high mobility group box 1 (HMGB1).

Hypoxia, and specifically HIF-1, is a potent and rapid inducer of the proinflammatory cytokine macrophage migration inhibitory factor (MIF). MIF, in turn, is a key regulator of the hypoxia-induced HIF-1α protein expression involving the MIF receptor CD74, thus forming an autocrine positive-feedback loop. Under hypoxia, MIF is released from intracellular stores and induces signaling cascades via CD74 to promote hypoxia-induced expression/stabilization of HIF-1α. HIF-1α is imported into the nucleus and dimerizes with its partner HIF-1β to induce HIF-1 target genes, such as MIF itself. This autoamplifying feedback loop is interrupted by high doses of anti-inflammatory glucocorticoids (GCs) via the GC receptor (GCR) or the inhibition of HIF-1α expression/stabilization under normoxia.

MIF acts on macrophages to induce release of many proinflammatory mediators, such as IL-6, and serves as the upstream regulator of TNF-α. MIF's function is unique among cytokines and its effects extend to multiple processes fundamental to tumorigenesis such as tumor proliferation, evasion of apoptosis, angiogenesis and invasion. These pleiotropic functional aspects are paralleled by MIF's unique signaling properties, which involve activation of the ERK-1/2 and AKT pathways and the regulation of JAB1, p53, SCF ubiquitin ligases and HIF-1. These properties reflect features central to growth regulation, apoptosis and cell cycle control. The significance of these pro-tumorigenic properties has found support in several in vitro and in vivo models of cancer and in the positive association between MIF production and tumor aggressiveness and metastatic potential in a variety of human tumors.

Furthermore, both MIF and TNF-α have been shown to impair erythroid colony formation, MIF activates HIF-1α under hypoxic conditions, which serves to activate a pro-angiogenic transcriptional program that is necessary for tumor progression. MIF downregulates the NK cell receptor NKG2D, thereby impairing NK cell cytotoxicity toward tumor cells and upregulating the anti-angiogenic factor thrombospondin-1.

In healthy subjects, the vagus nerve senses inflammation and significantly and rapidly inhibits such inflammation by releasing the neurotransmitter acetylcholine. Action potentials transmitted in the vagus nerve activate the efferent arm (the Cholinergic anti-inflammatory pathway) of the Inflammatory Reflex, the neural circuit that converges on the spleen to inhibit the production of TNF and other cytokines by macrophages there. Upon excitation, the vagus nerve releases acetylcholine. The vagus nerve and cholinergic agonists inhibit systemic inflammation by activating the noradrenergic splenic nerve via the α7 nicotinic acetylcholine receptor subunit (α7nAChR). α7nAChR is a member of the family of ligand-gated ion channels. After combining with acetylcholine, this ligand binding receptor transmits cholinergic anti-inflammatory signals into the cytoplasm to activate Janus kinase 2 (JAK2). The phosphorylation of JAK2 then triggers phosphorylation of signal transducers and activators of transcription 3 (STAT3) and promotes its dimerization. The phosphorylated STAT3 translocates from the cytoplasm into the nucleus. STAT3 then acts as a competitor to NF-κB to bind DNA, which results in a decrease in the production of pro-inflammatory cytokines, including TNF-α, high mobility group box 1 protein (HMGB1), macrophage inflammatory protein-2 (MIP-2), and IL-6. Acetylcholine also augments the production of prostacyclin ($PGI_2$), a potent vasodilator and anti-inflammatory molecule.

However, under pathological conditions the inflammatory reflex may be deficient. In such patients, overstimulation of pro-inflammatory cytokines may induce anemia by suppression of erythroid colony formation (MIF/$TNF_\alpha$/IL-1β) on the one hand and impairment of iron utilization (IL-6/hepcidin) on the other. Forms of anemia that are caused by insufficient numbers of EPO-sensitive erythroid colony-forming unit (CFU-E) cells do not respond well to EPO.

HMGB1 is a late cytokine mediator of the systemic inflammatory response. Increased plasma levels of HMGB1 have been shown to occur 12-24 hours after an increase in TNF-α levels, HMGB1 can then induce macrophages, neutrophils, and endothelium to amplify the pro-inflammatory cytokine cascade, MHGB1 can interact with toll-like receptors and the receptor for advanced glycation end products that further activate innate immune responses. These mediators activate infiltrating macrophages and endothelium, further increasing the release of HMGB1 as well as other cytokines, including TNF-α.

The inflammatory response also causes high levels of NO (nitric oxide) to be produced after iNOS (inducible nitric oxide) expression is induced, mainly in macrophages. NO reacts with concomitantly produced superoxide anions, thereby generating highly toxic compounds such as peroxynitrite and hydroxyl radicals.

Interaction Between Erythropoiesis and the Inflammatory Response

EPO and TNF-α have been shown to regulate each other in the hematopoietic system. EPO regulates TNF-α levels and erythropoiesis is inhibited by TNF-α. The circulating concentration of EPO has been shown to initially greatly increase (the plasma level of EPO may rise 1000-fold) following an anemic or hypoxaemic stimulus and subsequently declines despite continued hypoxia, likely due to the counteraction of this inflammatory response. In vivo administration of LPS and IL-1 has been shown to inhibit hypoxia-induced renal EPO mRNA levels in plasma EPO in rats, IL-1 has been shown to strongly activate NF-κB, which is a likely suppressor of the EPO promoter. In addition, during inflammation, hepatocyte nuclear factor 4 (HNF-4), a positive transcription factor, is lowered and GATA-2, a negative regulating transcription factor, is elevated. TNF-α produced during hypoxia profoundly inhibits apoptosis of polymorphonuclear cells (PMNs). Apoptosis of PMNS is a fundamental mechanism to halt inflammation.

Excessive inflammatory cytokine production acts to interfere with EPO activity in the bone marrow, reduces iron supply to the bone marrow, and upregulates the production of white blood cells, causing fewer stem cells to differentiate into red blood cells. A decrease in serum albumin concentration may signal the presence of inflammation.

The Spleen

The spleen is a major source of the initiation of systemic inflammation via the production of inflammatory cytokines. Electric stimulation of the splenic nerve induces norepinephrine release from the spleen. Efferent vagal nerve stimulation has been shown to stimulate release of acetylcholine in the celiac-mesenteric ganglia which activates postsynaptic α7nAChR of the splenic nerve, which in turn leads to the release of plasma and splenic norepinepherine in the spleen. Splenic norepinepherine inhibits cytokine production in splenic macrophages. The vagus nerve innervates the celiac ganglion, the site of origin of the splenic nerve.

Noradrenergic nerve fibers distribute with the vascular systems and innervate the perarteriolar lymphatic sheath, the marginal sinus, and the parafollicular zone. At the marginal sinus, tyrosine hydroxylase-positive fibers run adjacent to macrophages, suggesting a direct correlation between epinephrine release from the nerve terminal and the macrophages associated with them.

There is both structural and functional evidence of a neural reflex pathway between the spleen and the kidneys (the splenorenal neurogenic reflex). Stimulation of the afferent sympathetic nerves of the spleen results in activation of the efferent sympathetic nerves of kidneys and increases blood pressure. This reflex is not active after renal denervation or after administration of Angiotensin II inhibitors, indicating that that the reflex is limited to the splanchnic region and does not elicit a general increase in sympathetic nerve activity.

Activation of the Renin-Angiotensin System

Stimulation of the sympathetic nerves of the kidney causes arteriolar vasoconstriction leading to an increase in EPO and renin production, a decrease in GFR, and a decrease in RBF. Renin production leads to the production of angiotensin II through the renin-angiotensin system (RAS). Angiotensin II in turn has been found to increases erythropoietin secretion by reducing renal blood flow and increasing proximal tubular reabsorption (i.e., altering peritubular oxygen tension). Angiotensin II may also have direct stimulatory effects on bone marrow erythrocyte precursors. Further angiotensin II has been shown to constrict efferent arterioles of the kidney, while having no effect on the afferent arterioles, leading to renal hyperfiltration and greater GFR. Hyperfiltration can take place in a single nephron even with globally decreased GFR. In advanced chronic kidney disease, all remaining nephrons hyperfilter.

Activation of RAS is associated with increases in blood pressure and enhanced $O_2^-$ (oxidative stress) activity, which has been shown to cause a reduction of NO availability leading to a disparity between oxidative and antioxidative mechanisms in the tissues, in turn leading to many pathological states. Angiotensin II stimulates renal release of sympathetic neurotransmitters, e.g., norepinepherine, which may further exacerbate sympathetic overstimulation.

Oxygen Sensing

Oxygen sensing in the kidneys takes place in the juxtamedullary cortex and outer medulla where specialized interstitial cells called renal Epo-producing and oxygen-sensing (REPOS) cells respond to hypoxia (decreased tissue $PO_2$). Oxygen sensing in the kidney may be affected by changes in concentration of oxygen, iron, divalent metal ions, ascorbate, reactive oxygen species, tricarboxylic acid cycle intermediates, and nitric oxide (NO).

Renal Blood Flow

Renal blood flow (RBF) is determined by the difference between renal artery pressure and renal vein pressure divided by the total renal vascular resistance. Most of the renal vascular resistance resides in three major vascular segments: the interlobular arteries, afferent arterioles, and efferent arterioles. Resistance of these vessels is determined by the sympathetic nervous system, as well as by various hormones and a local internal renal control mechanism. If renal artery and renal vein pressure remain constant, a decrease in vascular resistance in any of the vascular segments increases RBF, while an increase in resistance tends to reduces RBF.

Input from the sympathetic nervous system triggers vasoconstriction of the renal artery and kidney, thereby reducing renal blood flow. The parasympathetic nervous system inhibits the sympathetic nerves of the renal artery and kidney and trigger vasodilation, thereby increasing renal blood flow. The sympathetic signals travel through the sympathetic trunk ganglia, where some may synapse, while others synapse at the aorticorenal ganglion and the renal ganglion.

Vasoconstriction of the preglomerular afferent arteriole will decrease RBF and glomerular filtration. Increasing postglomerular resistance by constriction of the efferent arteriole, in contrast, augments glomerular filtration and reduces RBF. Finally, combined vasoconstriction of afferent and efferent arteriolar dramatically reduces RBF without such pronounced changes in filtration.

Intense sympathetic nerve stimulation is required to constrict the arterioles and decrease RBF. Under normal conditions, moderate or mild sympathetic nerve stimulation will not have an effect on RBF. More subtle increases in renal nerve activity increase renal tubular sodium reabsorption and increase renin secretion without changes in renal hemodynamics.

The kidneys can endure a relatively large reduction in renal blood flow before actual damage to the renal cells occurs. As long as renal blood flow does not fall below about 20 percent of normal, acute renal failure due to hypoxia can usually be reversed if the cause of the ischemia is corrected before damage to the renal cells has occurred. This ischemic state should not be maintained longer than a few hours to avoid intrarenal acute renal failure.

Under normal conditions, renal blood flow remains relatively constant even with large fluctuations in arterial blood pressure ranging between 80 and 170 mm Hg due to feedback mechanisms intrinsic to the kidney. The kidneys have a feedback mechanism that links changes in sodium chloride concentration at the macula densa with the control of renal arteriolar resistance. The purpose of this feedback mechanism is to ensure a relatively constant delivery of sodium chloride to the distal tubule and prevent spurious fluctuations in renal excretion. The macula densa cells sense fluctuations in sodium chloride concentrations and initiate a signal that both alters the resistance of the afferent arterioles and affects the release of renin, thereby affecting the resistance of the efferent arterioles.

Chronic Overstimulation of Sympathetic Renal Nerves

The chronic reduction of renal blood flow, increase in GFR (glomerular hyperfiltration), oxidative stress, and inflammatory cytokines, as a result of overstimulation of the renal sympathetic efferent nerves leads to loss of renal function as a result of renal ischemia. Loss of renal function not only results in the reduction in the number of cells capable of producing EPO, but also a dampening of the kidney's ability to sense hypoxic conditions resulting from a lower GFR due to ischemic injury to renal tubules. Since less oxygen is consumed in the renal cortex due to a lower GFR, the local relative excess of oxygen in the renal cortex results in the down-regulation of EPO production. There is evidence that demonstrates a downward trend toward lower hemoglobin levels and a reduction in EPO effectiveness or production at lower levels of GFR.

Thus sympathetic overstimulation can lead to damage of the kidneys that results in both an inability to sense anemia and an inability to produce EPO.

In addition, after chronic overstimulation of the renal sympathetic nervous system, red blood cell production may also be inhibited by the resulting inflammatory response, as discussed above. The inflammatory response may further exacerbates the anemia by, e.g., leading to the sequestration of iron from bone marrow. Chronic kidney disease is characterized by elevated circulating levels of inflammatory cytokines such as interleukin 6, which can both impair bone marrow function and significantly alter iron metabolism.

Nitric Oxide

Nitric oxide (NO) has been shown to induce HIF-1 activation via stabilization of HIF-1α. NO is also a potent vasodilator. NO acts to vasodilate the afferent arterioles. NO is a powerful inhibitor of eryptosis (programmed death of anucleic red cells), Eryptosis is enhanced in a variety of clinical conditions associated with low levels of nitric oxide, such as heart disease, diabetes, renal insufficiency, sickle-cell anemia, and thalassemia.

Activation of parasympathetic nitrergic nerves (wherein NO mediates transmission) innervating renal vasculature contributes to vasodilatation in renal arteries and pre- and postglomerular arterioles, an increase in renal blood flow, and a decrease in vascular resistance. NO from neurons in the brain acts on the paraventricular nucleus of the hypothalamus and the rostral ventrolateral medulla and inhibits the central sympathetic nerve activity to the kidney, leading to renal vasodilatation and increased renal blood flow.

Under pathological conditions (e.g., during inflammation), high levels of NO are produced after iNOS (inducible nitric oxide) expression is induced, mainly in macrophages. But this NO reacts with concomitantly produced superoxide anions, thereby generating highly toxic compounds such as peroxynitrite and hydroxyl radicals.

The efferent arteriole endothelium contains nNOS (neuronal NO synthase) and eNOS (endothelial NO synthase). The renal nerves found in perivascular connective tissue and near the pelvic epithelium also contain nNOS. In addition, there are nNOS-containing neurons in sympathetic preganglionic neurons in the spinal cord, Several of the homeostatic actions of spinal afferents are brought about by the release of the transmitters NO and calcitonin gene-related peptide (CORP) from their peripheral endings.

Autonomic Nervous System

Patients with severe autonomic failure have a high incidence of anemia. Up to 38% of these patients are anemic (hemoglobin <120 g/liter for women and <130 g/liter for men) without an obvious cause. The autonomic nervous system controls the involuntary smooth and cardiac muscles and glands throughout the body, serving the vital organ systems such as the heart and kidneys that function automatically. The two divisions (sympathetic and parasympathetic) of the autonomic nervous system oppose each other in function, thus maintaining balance. Both pathways include afferent pathways (from a receptor or an organ to the central nervous system) and efferent pathways (acting in the opposite direction) that relate to erythropoiesis. Signals transmitted via the parasympathetic fibers of the vagus nerve generate an anti-inflammatory response, while signals traveling along the sympathetic fibers initiate erythropoiesis and the inflammatory response.

Under normal physiological conditions, vagal tone (parasympathetic activation) predominates over sympathetic tone at rest. Abrupt or intense parasympathetic nerve discharge will inhibit tonic sympathetic activation in dynamic states, such as exercise.

Sympathetic Withdrawal

Sympathetic failure can contribute to anemia by blunting of the expected compensatory erythropoietin response. The reticulocyte response to acute bloodletting was greatly diminished in rats when their kidneys were functionally denervated. The lack of sympathetic stimulation results in decreased erythropoietin production and development of anemia in patients with autonomic failure. The magnitude of sympathetic impairment correlates with the severity of anemia.

Overdrive of the Sympathetic Nervous System

Hypertension, heart failure, CHF, advanced cancer, and chronic renal disease, are a few of many disease states that can result from chronic over-activation of the sympathetic nervous system (SNS) and/or vagal withdrawal. Chronic activation of the SNS is a maladaptive response that drives the progression of these disease states, together with anemia as a common comorbidity. Although EPO production may initially be enhanced, because of the resulting inflammation and/or kidney damage, together with other resulting aggravating factors, anemia often results with the progression of these disease states. In addition, sympathetic over activity has been shown to blunt peripheral chemoreceptor function, which in turn increases sympathetic activity.

The Observed/Predicted Ratio

In certain embodiments, the etiology of the anemia is determined by determining the EPO observed/predicted (O/P) ratio. The observed EPO may be determined by quantifying the serum EPO level. The predicted EPO level is determined from determining the serum hemoglobin level and correlating the observed hemoglobin level with an EPO level that would be normal based on a reference population. An O/P ratio of 1 suggests that endogenous EPO production is as expected from the hemoglobin level. A value below 1 suggests that endogenous EPO production is lower than expected. A value above 1 suggests that endogenous EPO production is higher than expected. An O/P<0.916 may be defined as lower than expected. An O/P>1.087 may be defined as higher than expected.

Iron-Restricted Erythropoiesis

Chronic inflammation can lead to inefficient iron handling and entrapment in the reticuloendothelial system. Thus in some patients, anemia is caused by the inefficient handling of iron due to inflammation, rather than iron deficiency. In certain embodiments, the patient's O/P ratio, transferrin saturation, and ferritin levels are determined and used to diagnose the etiology of the anemia. Iron-restricted erythropoiesis diagnosed in patients who have high O/P levels, and low transferrin saturation (e.g., <20%-25%) without very high ferritin (e.g., <1,200 ng/mL).

Patients Having Higher than Expected EPO Levels

Higher than expected EPO levels have been observed in a relatively small but significant percentage of anemic CHF patients and are strongly associated with a higher mortality compared to anemic CHF patients with expected or lower than expected EPO levels, independent of hemoglobin levels.

Higher than expected EPO levels have also been observed as a primary response in patients after intense chemotherapy.

Mechanistically, patients with higher than expected EPO levels are capable of producing endogenous EPO. It has been shown that serum of CHF patients inhibits the proliferation of bone marrow derived erythropoietic cells from healthy volunteers, indicating that serum factors induce insensitivity to endogenous EPO. Such erythropoietin resistance may be due to the pathogenetic triad of iron-restricted erythropoiesis, inflammation, and bone marrow suppression.

Heart Failure

In heart failure (HF) patients, anemia has been found to be due to chronic disease (i.e., unresponsiveness to erythropoietin, due, at least in part, to chronic inflammation), kidney disease, overstimulation of the renin-angiotensin system, hemodiluation, and a deficiency in iron available for erythropoiesis.

Erythropoietin plasma levels increase progressively with deteriorating cardiac function in patients with HF. Inflammation appears to be the dominant source of anemia in ischemic HF; neurohormonal factors appear to play the largest role in non-ischemic HF.

Several parameters of cardiac failure have been shown to improve with correction of the anemia with subcutaneous erythropoietin in combination with iron. Correction of anemia has a major effect on improving cardiac function as reflected by an improvement in left ventricular ejection fraction, a reduction in cardiac dilation and hypertrophy, a reduction in β natriuretic peptide levels, and an increase in oxygen utilization during maximal exertion.

Congestive Heart Failure

Endogenous EPO levels are comparable between anemic and nonanemic congestive heart failure (CHF) patients and are generally elevated proportional to the severity of symptoms. Sympathetic overactivity may be triggered or exacerbated by chemoreceptor dysregulation associated with fluid and electrolyte shifts associated with CHF. More specifically, the renal sympathetic nerves, along with cardiac sympathetic nerves, have been shown to be overstimulated in CHF. Blood flow to the kidneys has also been shown to decrease. In addition, CHF is characterized by an elevation in plasma levels of proinflammatory cytokines, notably IL-6 and TNF-α, while the potent pro-anti-inflammatory cytokines IL-10 has been shown to be reduced.

Stimulation of the renin-angiotensin system as a result of increased sympathetic stimulation and decreased renal perfusion results in further arteriolar vasoconstriction, sodium and water retention, and release of aldosterone. Release of aldosterone leads to sodium and water retention, endothelial dysfunction, and organ fibrosis. Baroreceptor and osmotic stimuli cause the hypothalamus to release vasopressin. Vasopressin causes reabsorption of water in the renal collecting duct.

Approximately one-third of CHF patients are anemic. Although erythropoietin levels do not correlate well with hemoglobin levels in most anemic CHF patients, it has been shown that patients with persistently high erythropoietin levels had significantly lower hemoglobin levels. The vast majority (reportedly greater than 90%) of anemic CHF patients, however, have a significantly low O/P ratio, indicative of an impairment in EPO production. The cause of this impairment may be attributed to a combination of decreased renal function and a direct inhibition of EPO production by cytokines.

Chronic kidney insufficiency (CKI), which may result from renal ischemia and inflammation due to prolonged overstimulation of renal sympathetic nerves, is present in about half of all CHF cases and is the most common cause of anemia in CHF patients. CKI is associated with a lower GFR and thus both EPO production and the ability to sense hypoxia may be deficient. Fluid retention, and consequently haemodilution, due to activation of the renin-angiotensin system (RAS), is also a source of anemia in CHF patients.

While CHF is infrequently associated with biochemical indices of impaired iron supply, iron supplies in the bone marrow are often significantly depleted. Hepcidin, a peptide synthesized by the liver, is a key regulator of iron metabolism. Hepcidin is a hormone that lowers serum iron levels and regulates iron transport across membranes, preventing iron from exiting the enterocytes, macrophages, and hepatocytes. The action of hepcidin is mediated by binding to the iron exporter ferroportin. Hepcidin expression in the liver is dependent on the protein hemojuvelin.

Inflammation leads to increased hepcidin production via IL-6, whereas iron deficiency and factors associated with increased erythropoiesis (hypoxia, bleeding, hemolysis, dyserythropoiesis) suppress the production of hepcidin. IL-6 stimulates hepcidin gene transcription, most notably in the hepatocytes. Studies involving human hepatocyte exposure to a panel of cytokines showed that IL-6, but not TNFα or IL-1, induced the production of hepcidin mRNA.

Cancer

Anemia in cancer has been shown to be due to impaired erythropoiesis (production of red blood cells) and relatively inadequate EPO production, as evidenced by significantly lower O/P EPO. RAS is known to contribute to the regulation of tumour growth in several types of malignancy. Angiotensin II is a cytokine that acts as a growth factor for tumors and increases oxidative stress. Angiotensin II type-1 and type-2 receptors (AT1R and AT2R) are involved in the regulation of cellular proliferation, angiogenesis, and tumour progression. Angiotensin II levels have been found to be elevated in cancer patients. NO also enables or enhances angiogenesis. Angiogenic growth factors such as vascular endothelial growth factor (VEGF) and fibroblast growth factor (FGF) induce NO and require NO to elicit an effect. NO modifies the release of cytokines from macrophages. The serum levels of MIF, TNF-α, and IFN-gamma have been found to be significantly higher in anemic cancer patients than those in healthy controls or in nonanemic cancer patients. These inflammatory cytokines, along with others have been found to play a major role in the pathophysiology of anemia in cancer patients. Inflammatory cytokines and chemokines promote growth of tumor cells, perturb their differentiation, and support the survival of cancer cells. Down regulation of proinflammatory cytokines, such as TNFα, IL-6 and IL-1k, or transcription factors that are required for signaling by these cytokines, including NF-kB and STATs, are potential targets for both anticancer and anemia therapy.

Cancer, as well as cancer treatments such as chemotherapy, is frequently associated with kidney malfunction and lower GFR. It has been reported that between 12% and 49% of critically ill cancer patients experience acute renal failure and 9% to 32% require renal replacement therapy during their intensive care unit stay.

Renal Denervation

A bilateral nephrectomy, which inherently includes renal denervation, is known to reduce blood pressure better than hypertensive medication currently available, and reduce blood pressure even in refractory/resistant hypertensive patients (patients wherein more than three hypertensive medications failed to control blood pressure). See, e.g., Zazgornik, Bilateral Nephrectomy: The Best, but Often Overlooked Treatment for Refractory Hypertension in Hemodialysis Patients (1998), incorporated herein by reference in its entirety. Renal denervation by bilateral nephrectomy is known to affect a cure for hypertension, i.e., eliminate the patient's dependency of hypertensive medications to lower blood pressure. Renal denervation by bilateral nephrectomy, splanchnicectomy, and other more drastic sympathectomies is known to reverse cardiovascular diseases, including resulting in reverse remodeling of the heart (wherein the heart becomes healthy again) and a decrease in the likelihood of strokes. Renal denervation, whether by bilateral nephrectomy, intravascular radiofrequency ablation, or laparoscopic denervation, is known to be safe, i.e., it does not result in the collateral damage of a more extreme sympathectomy, e.g., a splanchnicectomy wherein patients were found to often suffer from orthostatic hypotension, arterial hypotension, erectile dysfunction, etc.

Renal denervation by bilateral nephrectomy is known to improve GFR, i.e., kidney function of the transplanted kidneys. Thus a renal denervation may actually be beneficial to the kidney's inherent ability to produce EPO. In small, proof-of concept studies in humans, incomplete renal denervation was also shown to stabilize, or at least slow, the progressive decline of GFR in most subjects, although some patients had a decrease in eGFR of more than a 25% at six months. See, e.g., G. Thomas, et al., Renal denervation to treat resistant hypertension: Guarded optimism, Cleveland Clinic Journal of Medicine, 79(7):501-510 (2012): D. Hering, Renal Denervation in Moderate to Severe CKD, JASN ASN.2011111062 (2012); G. Simonetti, et al., Endovascular Radiofrequency Renal Denervation in Treating Refractory Arterial Hypertension: a Preliminary Experience, Radiol Med, 117(3):426-44. (April 2012). Probable mechanisms by which renal denervation exerts this renoprotective effect include the blood pressure lowering effect, a decline in the release of renin and adenosine, a resetting of the baroreceptors, and a decrease in neurogenic inflammation. Hypertension may lead to lesions in the kidney. Renin leads to the production of Angiotensin II which constricts the efferent arterioles of the kidney and can lead to hyperfiltration. Angiotensin II is also a pro-inflammatory. Blockade of $A_1$ adenosine receptors in the kidney has been shown to maintain GFR and increase renal blood flow. After chronic hypertension, the baroreceptors get reset so that the threshold for baroreceptor activation is at a higher blood pressure, allowing for sympathetic nerve stimulation. Norepinephrine acts on $\alpha_1$ and $\alpha_2$ adrenergic receptors and proinflammatory neuropeptide substance P exhibit proinflammatory properties. Proinflammatory cytokines such as TNF-α and IL-1β can either directly reach the central nervous system via the circulation or alternatively stimulate peripheral afferent nerve fibers, thereby activating central neurons in specific brain areas and probably also autonomic efferent nerves.

However, complete renal denervation, e.g., by a bilateral nephrectomy, in some, but not all patients, results in anemia. Although renal denervation has been found to diminish response to varying oxygenation and carbon dioxide in kidney transplant patients, i.e., patients having denervated kidneys, the renovascular response was not totally abolished. The post-renal transplant patients had a response to hypercapnia ($CO_2$) that was about 50-55% of the change observed in non-denervated humans.

One study of 15 human patients with stage 3 and 4 chronic kidney disease (mean eGFR 31 mL/min/1.73 $m^2$) subjected to radio frequency intravascular catheter renal denervation showed a nonsignificant trend towards increased hemoglobin levels. Acute renal denervation has not shown to affect levels of mRNA encoding erythropoietin in animals. Italo Biaggioni, *Erythropoitin in Autonomic Failure*, Primer on Autonomic Nervous System, Chapter 115, p. 421. This indicates that, in addition to renal nerves, other factors such as circulating catecholamines and neuropeptides also contribute to the renovascular response in humans.

Implantable Body Fluid Analyzer

In an embodiment, an implantable microarray device is used to measure levels of EPO, nitric oxide, hemoglobin, hepcidin, hemocrit, iron, proinflammatory cytokines, anti-inflammatory cytokines, renin, MIF, CK-MB, cTnT, cTnI, platelets, blood glucose, creatinine, etc. An example of such an implantable microarray device suitable for use is disclosed in Koh et al. U.S. Pat. No. 8,192,360, incorporated herein in its entirety. Koh discloses an exemplary implantable microarray device that includes an inlet for a body fluid, a plurality of individual reaction cell arrays where each reaction cell array includes a series of reaction cells configured to receive the body fluid, a sensor array to sense a reaction result for an individual reaction cell array where the reaction result corresponds to a reaction between the body fluid and at least one reagent in each of the reaction cells of the individual reaction cell array and a positioning mechanism to position an individual reaction cell array with respect to the sensor array.

Determining Renal Insufficiency

In certain embodiments, the level of renal function of the patient is measured in order to determine a treatment strategy. In certain embodiments, the level of renal function of the patient is monitored in order to provide feedback to a neuromodulation device.

Early renal insufficiency (ERI), defined as a calculated or measured glomerular filtration rate (GFR) between 30 and 60 mL/min per 1.73 m$^2$. If the filtering of the kidney is deficient, creatinine blood levels rise. In certain embodiments, renal dysfunction is defined as a plasma creatinine >1.5 md/dL.

In an embodiment, the estimated glomerular filtration rate (eGFR) is measured using the abbreviated Modification of Diet in Renal Disease equation:

$$eGFR = 186.3 \times (creatinine/88.4)^{-1.154} \times (age)^{-0.203} \times (\times 0.742 \text{ if female}).$$

The estimated prevalence of at least moderate chronic kidney disease (defined as GFR <60 mL/min) in CHF populations is 20% to 40%. Heart failure and chronic kidney disease may be the result of a maladaptive response that chronically stimulates the sympathetic nervous system. Stimulation of the renal sympathetic nervous system increases the release of renin, increases sodium reabsorption, and reduces renal blood flow. In addition, patients suffering from chronic kidney disease may have ischemia of the kidneys. Although hypoxia of the kidneys may initially result in an increase in EPO, chronic hypoxia has been found to result in down-regulation of EPO due to resulting proinflammatory cytokines. In certain embodiments, the level of renal function is measured in order to determine whether the sympathetic renal nerves should be stimulated in order to enhance the production of EPO or whether such stimulation would instead lead to an exacerbation of the anemia. In patients diagnosed with renal insufficiency, vagal nerve stimulation in order to decrease systemic inflammation and increase NO production may be indicated by the device. In certain embodiments, a patient's vagal nerve is stimulated in order to upregulate anti-inflammatory cytokines and down regulate proinflammatory cytokines in patients found to have a chronically stimulated sympathetic nervous system or ischemic kidneys. In an embodiment, the renal sympathetic nerve is blocked via overstimulation in order to down-regulate the production of renin and proinflammatory cytokines.

According to certain embodiments, exogenous EPO may be administered using a drug pump, or through conventional administration. In certain embodiments wherein vagal stimulation or sympathetic block are used, less exogenous EPO may be used than otherwise required because of the mitigation of inflammation that would otherwise lead to EPO insensitivity.

Determining Iron Sufficiency

In certain embodiments, the patient's iron level is measured in order to determine a treatment strategy. In certain embodiments, the patient's iron level is monitored in order to provide feedback to a neuromodulation device.

Iron deficiency may be defined as ferritin <100 mcg/L and/or transferrin saturation (TSAT)≤20%. The ferritin level indicates the amount of iron stored in the body. In an embodiment, the target ferritin level is greater than about 100 mcg/L and less than about 800 mcg/L. TSAT indicates how much iron is actually available to make red blood cells. In an embodiment, a target TSAT score is between about 15-50% in male and postmenopausal female subjects and about 12-45% in premenopausal female subjects. Target serum iron levels may be between about 65-477 µg/dL in males and about 50-170 µg/dL in females. In iron deficient anemia, the serum iron levels are low, while the transferrin levels are high, due to the fact that the liver produces more transferrin in theory to maximize the use of the little iron that is available. In certain embodiments, a drug pump is used to provide adequate iron levels. In certain embodiments, the device uses the iron levels as an indication that vagal nerve stimulation should be used to decrease systemic inflammation.

Determining Vitamin D Sufficiency

In certain embodiments, a vitamin D deficiency is diagnosed when the vitamin D level drops below 20 ng/dL. It has been found that a vitamin D deficiency is associated with anemia independent of age, sex, race/ethnicity, with the odds of anemia being increased approximately 60% in the presence of vitamin D deficiency. In certain embodiments, a drug pump is used to provide an adequate vitamin D level.

Determining Folic Acid Sufficiency

In certain embodiments, a subject is diagnosed with a folic acid deficiency when the serum folate is ≤3 µg/L. In an embodiment, a subject is diagnosed with a folic acid deficiency when the erythrocyte folate level is ≤140 µg. In certain embodiments a drug pump is used to provide an adequate folic acid level.

Determining Vitamin B12 Sufficiency

In certain embodiments, a subject is diagnosed with a vitamin B12 deficiency when the serum level is ≤200 pg/ml. In certain embodiments, a subject is diagnosed with a vitamin B12 deficiency when the serum level is ≤500 pg/ml. In certain embodiments, a drug pump is used to provide an adequate vitamin B12 level.

Implanted Electrical Nerve Stimulation for Treatment of Anemia

According to certain embodiments, an internal stimulation device is used for hemoglobin maintenance in Heart Failure (HF) patients, cancer patients, patients who have undergone renal denervation, and/or a patient suffering from anemia caused by autonomic imbalance.

Nerve Stimulation

The smooth muscle layers of arteries are controlled by the sympathetic and parasympathetic nervous systems. Typically, the layer of smooth muscle between elastic lamina of an artery opens and closes the arterial lumen. Closing an arterial lumen is referred to as vasoconstriction and restricts blood flow; opening an arterial lumen is referred to as vasodilation and facilitates blood flow.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for sensing activity of and/or stimulation of autonomic nerves, non-myocardial tissue, other nerves, etc. For example, this lead may be positioned in and/or near a patient's heart or near an autonomic nerve within a patient's body and remote from the heart. Various examples described herein include positioning a lead proximate to the right and/or the left carotid sinus nerve for at least purposes of sensing nerve activity.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for sensing activity of and/or stimulating autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of sensing activity of and/or stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of sensing activity of and/or stimulating an autonomic nerve, non-myocardial tissue, other nerves, etc., wherein such an electrode may be positioned on the lead or a bifurcation or leg of the lead.

The device 100 may be implanted a various locations within the patient. For example, in certain embodiments the stimulation device 100 may be implanted subcutaneously in the pectoral region of a patient's chest.

The stimulation device 100 may take various forms. For example, in certain embodiments the stimulation device 100 may comprise a dedicated neurostimulation device.

Figure 2:
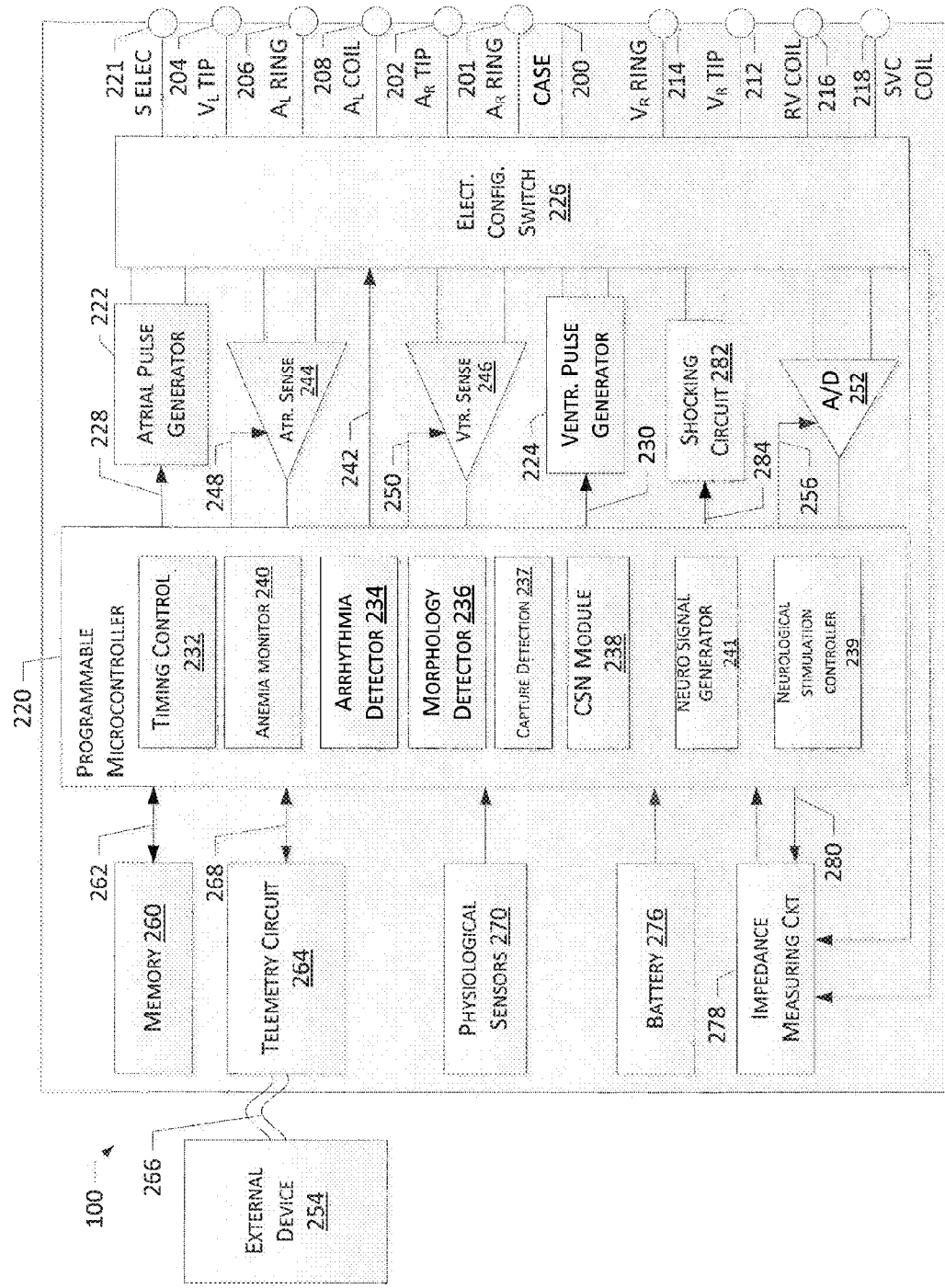
FIG. 2 is a functional block diagram of an exemplary stimulation device.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes, Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, a CSN module 238 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The CSN module 238 may perform a variety of tasks related to, for example, arterial blood chemical composition and/or arterial blood pressure. This component can be utilized by the stimulation device 100 in determining therapy in response to chemosensory and/or barosensory information. The CSN module 238 may be implemented in hardware as part of the microcontroller 220, or as software/firmware instructions programmed into the device and executed on the microcontroller 220 during certain modes of operation. The CSN module 238 may optionally implement various exemplary methods described herein. The CSN module 238 may interact with the physiological sensors 270, the impedance measuring circuit 278 and optionally other modules. One or more of the physiological sensors 270 are optionally external to a pulse generator yet can provide information to the microcontroller 220.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers, Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (ND) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals and/or other signals across any pair of desired electrodes. The data acquisition system 252 is optionally configured to sense nerve activity and/or muscle activity from muscles other than the heart.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, wave shape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

As already mentioned, the stimulation device 100 can further include or communicate with one or more physiologic sensors 270. The physiologic sensors 270 may be housed within the case 200, on the surface of the case 200 or external to the case 200. The one or more physiologic sensors optionally connect to the device 100 via one or more of the connectors or via other connectors. In some instances, a physiologic sensor may communicate with the microcontroller 220 via a wireless link. For example, a wristwatch physiologic sensor may communicate via electromagnetic radiation signals or other signals with a circuit in the device 100 (e.g., the telemetry circuit 264). Of course, an implantable physiologic sensor may also communicate with the device 100 via such communication means.

A physiologic sensor may be used to implement "rate-responsive" therapy where information sensed is used to adjust pacing stimulation rate according to, for example, the exercise state of the patient. A physiological sensor may be used to sense changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). The microcontroller 220 can respond to such information by adjusting any of the various pacing parameters (e.g., rate, AV Delay, V-V Delay, etc.) or anti-arrhythmia therapy parameters (e.g., timing, energy, leading edge voltage, etc.).

Further examples of physiologic sensors that may be implemented in conjunction with the device 100 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which patent is hereby incorporated by reference.

The one or more physiologic sensors 270 may optionally include one or more of components to help detect movement (via, e.g., a position sensor or an accelerometer) and minute ventilation (via an MV sensor) in the patient. Signals generated by the position sensor and MV sensor may be passed to the microcontroller 220 for analysis in determining whether to adjust the pacing rate, etc. The microcontroller 220 may thus monitor the signals for indications of the patient's position and activity status, such as whether the patient is climbing up stairs or descending down stairs or whether the patient is sitting up after lying down.

The device 100 additionally includes a battery 276 that provides operating power to all of the circuits shown in FIG.

2. For a device 100 which employs shocking therapy, the battery 276 is capable of operating at low current drains (e.g., preferably less than 10 µA) for long periods of time, and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium or other suitable battery technology.

As mentioned above, the device 100 may include several components that provide functionality relating to neurostimulation as taught herein. For example, one or more of the switch 226, the sense circuits 244, 246, and the data acquisition system 252 may acquire cardiac signals that are used by an IEGM processing component (not shown) to provide IEGM data. This IEGM data may be stored in the data memory 260. In addition, a neuro-signal generator 241 may generate neurostimulation signals as taught herein. Here, the microcontroller 220 may provide one or more control signals 230 to the neuro-signal generator 241 to control the timing (e.g., start and stop times) and other parameters (e.g., amplitude, waveshape, and frequency) of the neurostimulation signals.

The microcontroller 220 (e.g., a processor providing signal processing functionality) also may implement or support at least a portion of the neurostimulation-related functionality discussed herein. For example, an anemia monitor 240 may perform anemia-related operations as described above (e.g., determining whether a anemia condition or a anemia condition exists). In addition, a neurological stimulation controller 239 may perform neurostimulation operations such as, for example, determining which form of innervation to use based on the current anemic condition and the parameters for the neurostimulation signals.

The exemplary device 100 optionally includes a connector capable of connecting a lead that includes a pressure sensor. For example, a connector (not shown) optionally connects to a pressure sensor capable of receiving information pertaining to chamber pressures or other pressures. Pressures may be related to cardiac performance and/or respiration. Pressure information is optionally processed or analyzed by the neurostimulatory generator module 241.

Commercially available pressure transducers include those marketed by Millar Instruments (Houston, Tex.) under the mark MIKROTIP®. A study by Shioi et al., "Rapamycin Attenuates Load-Induced Cardiac Hypertrophy in Mice", Circulation 2003; 107:1664, measured left ventricular pressures in mice using a Millar pressure transducer inserted through the LV apex and secured in the LV apex with a purse-string suture using 5-0 silk. Various exemplary methods, devices, systems, etc., described herein optionally use such a pressure transducer to measure pressures in the body (e.g., airway, lung, thoracic, chamber of heart, vessel, etc.).

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available microelectromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

While an accelerometer may be included in the case of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Renal Nerve Modulation

The primary stimulus for increased EPO synthesis is tissue hypoxia caused by decreased blood oxygen availability. This hypoxia signal is received primarily in the kidney, which responds by increasing production and secretion of EPO. The EPO is transported to the bone marrow where it promotes proliferation and differentiation of red cells. As a result of this increased red cell production, the blood's oxygen carrying capacity increases, the stimulus of hypoxia is reduced, and EPO production is decreased to maintain a steady state.

In use, the lead 110 may be delivered to a renal vessel in proximity to neural tissue contributing to renal function, as explained in further detail below. The renal vessel may be a renal artery, vein or other vessel. In an embodiment, $O_2$ perfusion in the kidney is modulated to cause EPO release. According to this embodiment, sympathetic nerves of the kidney can be stimulated in order to decrease renal blood flow and decrease GFR by vasoconstriction of the renal arteries. The kidney cells that make EPO are specialized and are sensitive to low oxygen levels in the blood. These cells release EPO when the oxygen level is low in the kidney. EPO then stimulates the bone marrow to produce more red cells and thereby increase the oxygen-carrying capacity of the blood. Hypoxia and anemia are the fundamental stimulus for erythropoietin (EPO) production. Recent in vitro studies suggest that EPO secretion in response to hypoxia is regulated by adenosine in the kidney. Extracellular adenosine is derived mainly from phosphohydroiysis of adenosine 5_-onophosphate (AMP). Ecto-5_-nucleotidase (CD73), a ubiquitously expressed glycosyl phosphatidylinositol-anchored ectoenzyme, is the pacemaker of this reaction. Because of its transcriptional induction by hypoxia, CD73-dependent adenosine generation is particularly prominent during conditions of limited oxygen availability. Furthermore, recent studies have shown that the EPO-producing peritubular renal fibroblasts express high amounts of ecto-5-nucleotidase on their surface.

Methods of radiofrequency catheter ablation are described in U.S. Publication Nos. 2013/0218029, 2013/0085489, 201310245621, 2013/0090637, 2011/0118726, and 2011/0137298, each of which is incorporated herein by reference in its entirety. In certain embodiments, these ablation catheters are modified in order to provide renal nerve stimulation, either in addition to or as a substitute for ablation, U.S. Publication Nos. 2012/0290053 and 2012/0290024, each of which is incorporated herein by reference in its entirety, describe renal nerve modulation systems for treatment of hypertension that can be modified in accordance with certain embodiments in order to stimulate the production of EPO.

Figure 3A:
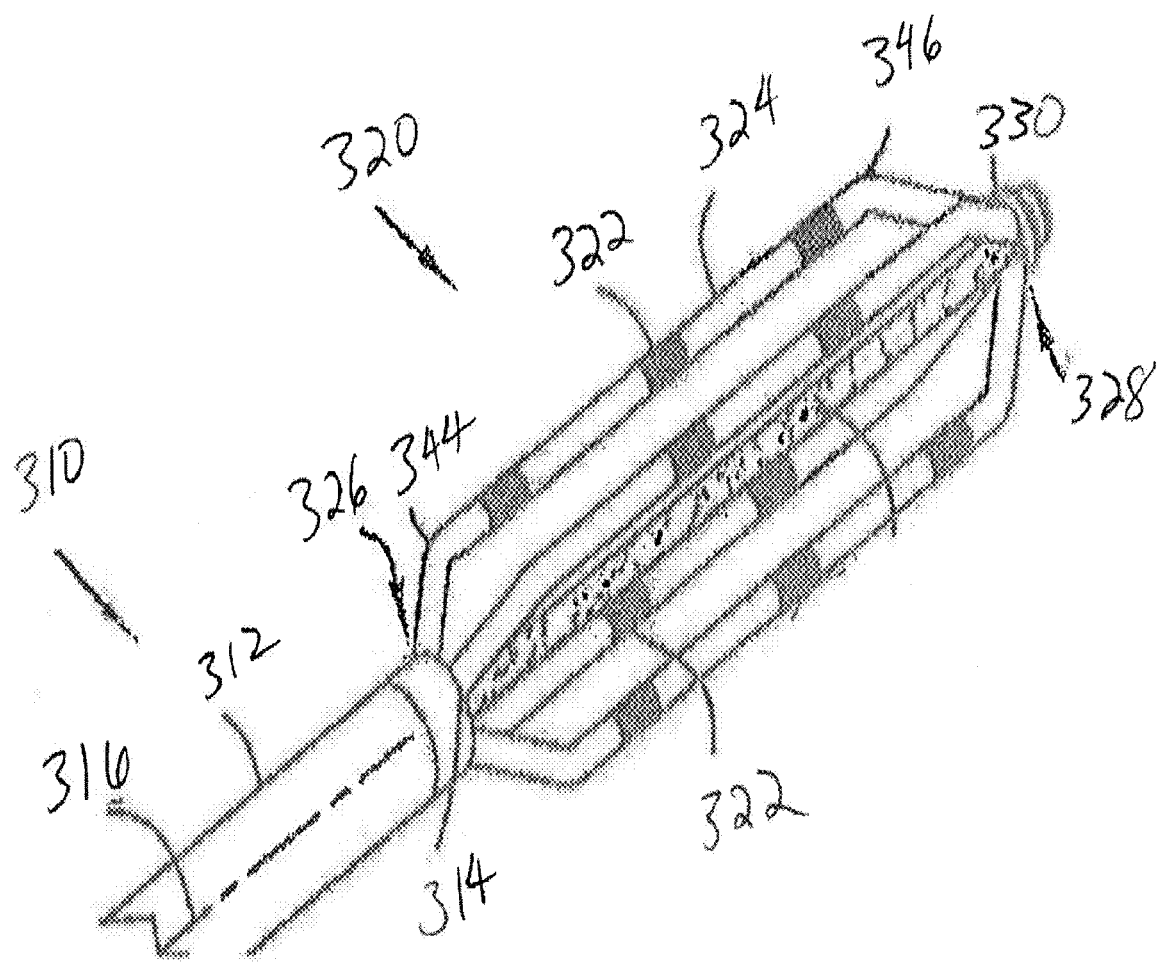
FIGS. 3A and 3B are perspective views of assemblies of ablation and/or neuromodulation elements for a catheter according to certain embodiments of the present invention.

FIG. 3A is a perspective view of a neurological lead 310 configured to stimulate EPO production. According to this embodiment, a neurological lead 310 includes an elongated catheter body 312 extending longitudinally between a proximal end (not shown) which connects to the neurological lead 310 and a distal end 314 along a longitudinal axis 316. A neuromodulation element assembly 320 includes a plurality of electrodes 322 connected to the catheter body 312. The electrodes 322 are discretely spaced from each other longitudinally and/or laterally. In certain embodiments, at least two of the electrodes 322 are spaced from one another longitudinally. In certain embodiments, the electrodes 322 are not spaced from one another longitudinally.

In certain embodiments, the electrodes 322 are configured for modulation (inhibition or stimulation) of the renal nerves, and/or to sense. The neuromodulation element assembly 320 can be configured to unipolar, bipolar, or multi-polar modulation. The modulation electrodes can be made of platinum-iridium (Ptir) or some other suitable electrode materials. Examples of sensing electrodes include sensors for sensing temperature, oxygen in blood, catheter tip force or pressure, blood pressure, blood flow, nerve activity, and impedance contact with the renal vein near the modulation electrode. The neuromodulation element assembly 320 has a terminal connector at the proximal end which is connected to a pulse generator. The neuromodulation element assembly 320 is preformed for fixation in the renal artery and/or vein and to achieve good electrode-tissue contact. Because the renal blood vessels (veins and arteries) are subject to displacement during respiration, the neuromodulation element assembly 320 includes a passive or an active fixation mechanism for fixation in the renal blood vessel. The neuromodulation element assembly 320 can utilize a variety of fixation mechanisms, different conductor designs, and different cross-sectional configurations.

As seen in FIG. 3A, the neuromodulation element assembly 320 may include a plurality of spines 324, which may be oriented generally longitudinally. Each spine 324 has a proximal end 326 connected to the catheter body 312 and a distal end 328. The distal ends 328 of the spines 324 are connected to a spine distal junction 330. Each spine 324 includes an intermediate segment 332, a proximal stiffness change between the proximal end 326 and the intermediate segment 332 of the spine 324, and a distal stiffness change between the distal end 328 and the intermediate segment 332 of the spine 324. The spines 324 include a plurality of electrodes 322 on the intermediate segments 332.

Figure 3B:
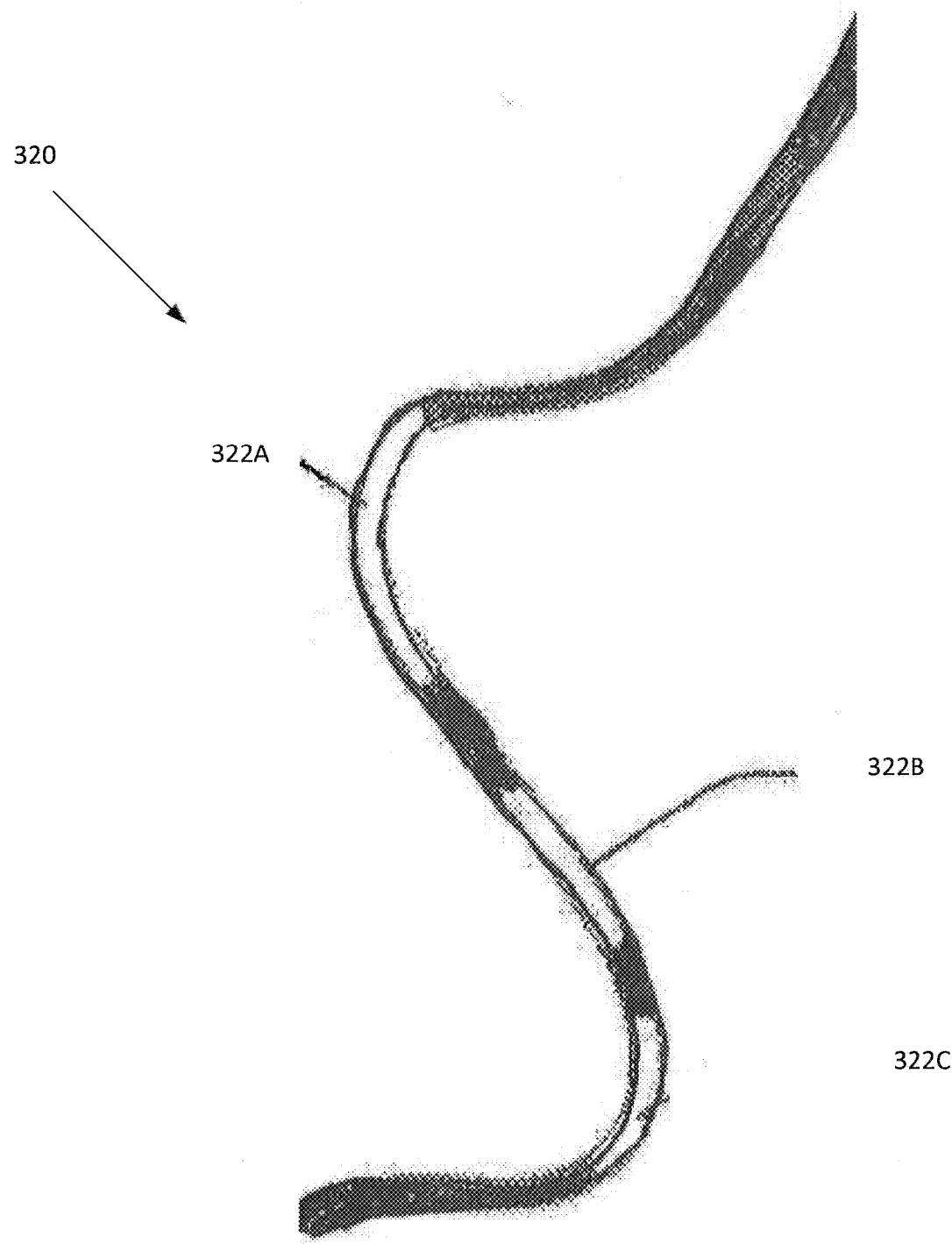

FIG. 3B illustrates an alternative embodiment, wherein the neuromodulation element assembly 320 has a helical configuration. A helix, sometimes also called a coil, is a curve for which the tangent makes a constant angle with a fixed line. The shortest path between two points on a cylinder (one not directly above the other) is a fractional turn of a helix (e.g., consider the paths taken by squirrels chasing one another up and around tree trunks). Helices come in enantiomorphous left- (coils counterclockwise as it "goes away") and right-handed forms (coils clockwise).

A helix is a space curve with parametric equations: $x=r*\cos(t)$; $y=r*\sin(t)$; and $z=c*t$, for t within a range of 0 to $2\pi$, where r is the radius of the helix and c is a constant giving the vertical separation of the helix's loops. Other equations exist to describe arc length, torsion, etc. Other possible configurations include, for example, sinusoidal or S-shaped, conical spirals, Poinsot's spirals, polygonal spirals, spherical spirals, semi-spherical spirals, slinky (e.g., spiral wound around a helix), stent-like, running or serial loop, etc.

In FIG. 3B the neuromodulation element assembly 320 includes a helical configuration that includes three electrodes 322a, 322b, and 322c. Such a neuromodulation element assembly 320 may include one or more electrodes. Such electrodes may act as anodes or cathodes. In general, the configuration acts to help secure the neuromodulation element assembly 320 at a particular location, for example, in an artery or vein.

Carotid Body and Sinus Stimulation

Various exemplary techniques described herein relate to the carotid body and the carotid sinus, U.S. Pat. No. 8,326,429, incorporated herein by reference in its entirety, describes therapeutic actions that may treat conditions such as sleep apnea, an increase in metabolic demand, hypoglycemia, hypertension, renal failure, and congestive heart failure. The carotid body is a small cluster of chemoreceptors and supporting cells located near the bifurcation of the carotid artery. It responds to changes in the composition of arterial blood, including the partial pressures of oxygen and carbon dioxide as well as pH, temperature and potassium concentration. The chemoreceptors responsible for sensing changes in blood gasses are called glomus cells. The carotid body is involved in both respiratory and cardiovascular control through complex neural pathways, for example, the carotid body provides for a reflex adjustment of respiration according to arterial blood chemistry. Hypoxia (decrease in $PO_2$), hypercapnia (increase in $PCO_2$), and acidosis (decrease in pH) increase the rate of chemosensory discharges in the carotid sinus nerve (CSN) and initiate ventilatory and cardiovascular reflex adjustments.

More specifically, the carotid body responds to a decrease in $PaO_2$ (e.g., atrial hypoxia), ischemia (e.g., from hypotension), an increase in $PCO_2$ (e.g., >10 mmHg), a decrease in pH (e.g., >about 0.1 to about 0.2 pH units), metabolic poisons (e.g., cyanide), drugs (e.g., nicotine, lobeline) and a decrease in blood glucose concentration.

While mechanisms underlying communication between glomus cells of the carotid body and petrosal ganglion neurons are not completely known, glomus cells, in response to natural and pharmacological stimuli, are expected to release at least one excitatory transmitter that generates discharges in the sensory nerve terminals of petrosal ganglion (PG) neurons.

The carotid sinus is a small oval bulge at the commencement of the internal carotid artery. At the carotid sinus, the arterial wall is thin and has a rich nerve supply from CN IX as well as some innervation from CN X. These nerves form an afferent limb of baroreceptor reflex changes in heart rate and blood pressure.

The regulation of arterial blood pressure involves negative feedback systems incorporating baroreceptors located in the carotid sinus and in the aortic arch. The carotid sinus nerve (CSN) branch of CN IX innervates the carotid sinus, which synapses in the brainstem. The aortic arch baroreceptors are innervated by the aortic nerve, which then combines with the vagus nerve (X cranial nerve) traveling to the brainstem. Arterial baroreceptors are sensitive to stretching of the walls of the vessels in which the nerve endings lie. Increased stretching augments the firing rate of the receptors and nerves, and recruits additional afferent nerves. The receptors of the carotid sinus respond to pressures ranging from about 60 mm Hg to about 180 mmHg.

A branch of CN IX innervates baroreceptors of the carotid sinus and chemoreceptors of the carotid body. This branch includes two sets of afferent fibers. One set ramifies in the wall of the carotid sinus (at the commencement of the internal carotid artery), terminating in stretch receptors responsive to systolic blood pressure: these baroreceptor neurons terminate centrally in the medial part of the nucleus solitarius. The second set of afferents in the carotid branch supplies glomus cells in the carotid body. These nerve endings are chemoreceptors monitoring blood chemistry. The central terminals enter the dorsal respiratory nucleus. More generally, the nerve supply to the carotid sinus and body is derived from the carotid branch of CN IX, branches to the carotid body from the inferior ganglion of CN X and sympathetic branches from the superior cervical ganglion.

Afferent nerve activity of CN IX due to a change in blood pressure, a decrease in blood oxygen concentration, a decrease in blood pH, and/or an increase in blood carbon dioxide concentration can cause corrective changes in ventilation so as to maintain blood gas and pH homeostasis.

Stimulation of the carotid chemoreceptors via hypoxic conditions has been found to affect renal hemodynamics. Hypoxia increases efferent renal activity and produces renal vasoconstriction.

Figure 4:
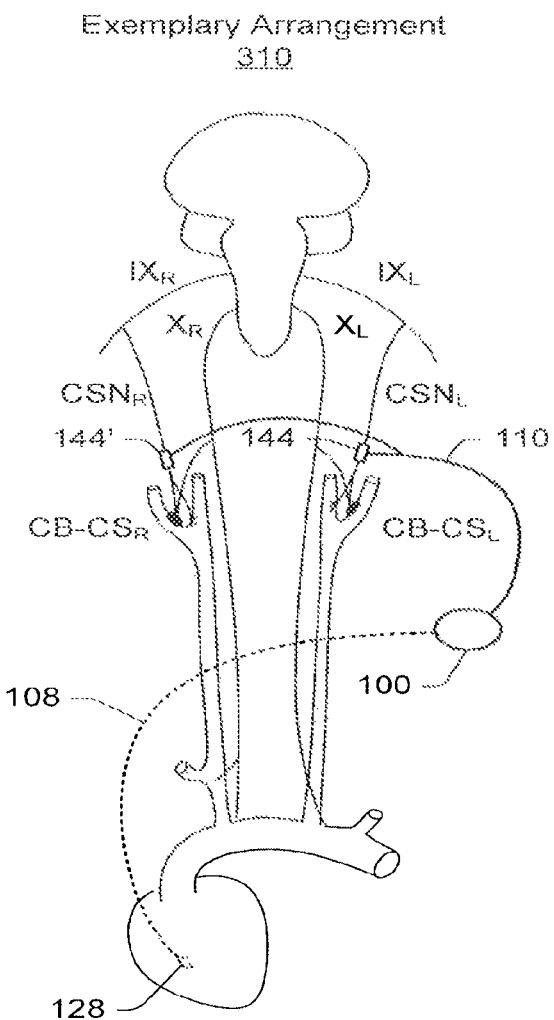
FIG. 4 is an approximate anatomic diagram that includes the right and left carotid body and sinus and an exemplary method for providing neural stimulation.

FIG. 4 shows an exemplary arrangement 410 of electrodes that can be used for both neuromodulation and sensing. The arrangement 410 is shown with reference to the heart, the brain, the aorta, the right common carotid artery and bifurcation, the left common carotid artery and bifurcation, the right carotid body and sinus ($CB\text{-}CS_R$), the left carotid body and sinus ($CB\text{-}CS_L$), and the ninth and tenth cranial nerves. The carotid arteries carry blood to the brain and innervation of the carotid body and sinus, which are located near the brain, allow the body to monitor blood flow and blood chemistry and respond accordingly. The tenth cranial nerve (CN X) is the vagus nerve and is primarily associated with parasympathetic activity. The vagus includes the right vagus ($X_R$) and the left vagus ($X_L$).

Various studies indicate that the vagus may innervate the carotid body while vagal innervation of the aortic baroreceptors is well established.

The arrangement 410 includes the implantable device 100 and a neuromodulation lead 110. The lead 110 includes one or more electrodes 144, 144' and may include a bifurcation that allows at least one electrode to be positioned at, or proximate to, each CSN. In the example of FIG. 4, the lead 110 includes a bifurcation where one branch of the lead allows for positioning the electrode 144' at the right CSN ($CSN_R$) and another branch of the lead allows for positioning the electrode 144 at the left CSN ($CSN_L$).

Figure 5:
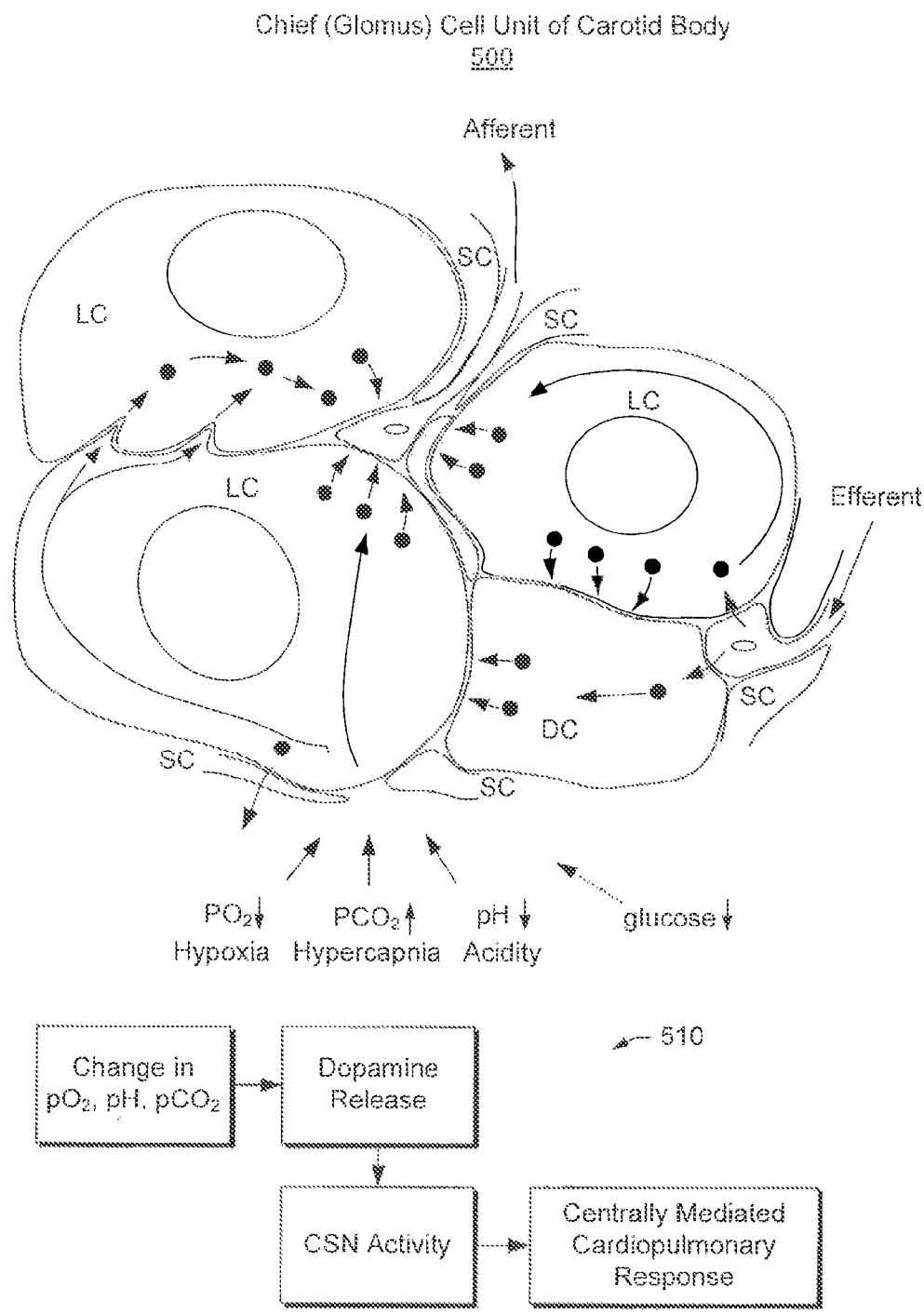
FIG. 5 is an approximate anatomical diagram of a unit of the carotid body responsive to chemical changes.

FIG. 5 shows a more detailed diagram of a cell unit of the carotid body 500 and a block diagram of a process 510. Sustentacular cells (modified Schwann cells, labeled SC) are intimately surrounded and interlaced with arch network of capillaries and venules. Clusters of cells are called "zellballen", and can generally be separated into "light" cell (labeled LC) and "dark" cell (labeled DC) subpopulations, referring to the density of intracellular neurosecretory granules. Chief cells are members of the amine precursor and uptake decarboxylase (APUD) family, recently referred to as the DNS (diffuse neuroendocrine system).

In an embodiment, a cell unit of a carotid body generates afferent nerve activity in response to a neuromodulation signal. For example, a neuromodulation signal in the process 510 can mimic a decrease in oxygen concentration, a decrease in pH and/or an increase in carbon dioxide, causing cells of the unit to release dopamine, which increases CSN activity and provokes centrally-mediated cardiopulmonary responses.

Spleen Stimulation

In certain embodiments, the spleen is electrically stimulated to release stored red cells to generate circulating signaling mechanisms of red cell shortage. Inhibitory or excitatory stimulation of the spleen's autonomic nerves would modulate blood flow to the organ, as well as control smooth muscle that maintains a small reserve of erythrocytes in the spleen. In certain embodiment, the spleen is electrically stimulated to vasoconstrict, reducing the flow of blood and lymph in an effort to block eryptosis.

Spinal Cord Stimulation

Renal sympathetic neurons originate in the thoracic and lumbar portion of the spinal cord (generally the area of T10-L1), and the ganglia are situated close to the spinal cord. In an embodiment, pre-ganglionic efferent nerves in the spinal cord in the area of T10-L1 are electrically stimulated. The pre-ganglionic efferent nerves communicate eventually to the kidney, or stimulate post-ganglionic nerves either at the appropriate sympathetic ganglia or nearer to the kidney. This stimulation is done to cause vasoconstriction in the arteries of the kidney, for temporary therapeutic reduction in renal blood flow. The effect is reduced oxygen delivery to the kidney. In an embodiment, the pre-ganglionic efferent nerves are stimulated intermittently and at appropriate time scale in order to create temporary hypoxia, thereby encouraging EPO production without causing ischemic injury, hypertension, or retention of waste products. In an embodiment, Angiotensin II receptor blockade is applied to prevent chronic blood pressure elevation and inflammation from intermittent hypoxia.

Brain Stimulation

Signals effecting erythropoiesis are generated in the hypothalamus and medulla oblongata within the brain. Electrical stimulation of the hypothalamic complex has been reported to induce increase in the number of circulating erythrocytes and reticulocytes, and in the hemoglobin levels. The diencephalon exerts its effect on anterior pituitary hormones through secretion of some neuroumoral substances transmitted to the hypophyseal cells by mean of the hupophysceal portal circulation. Stimulation of the hypothalamus has also been found to upregulate cytokine production. According to certain embodiments, the NF-κB pathway in the hypothalamus is blocked to reduce inflammation. In an embodiment, controlled hypothalamic deep brain stimulation is used to allow for regulation of erythropoiesis.

U.S. Pat. No. 6,978,180, incorporated herein by reference in its entirety, describes a neurological stimulation system adapted for implantation into a person's body for electrical, chemical, or combined electrical and chemical stimulation of target nerve tissue in the person's brain stem, that can be used in certain embodiments to increase EPO production and/or treat anemia. U.S. Pat. No. 7,313,442, incorporated herein by reference in its entirety, describes method and a system for using electrical stimulation and/or chemical stimulation that are used according to certain embodiments to stimulate, for example the hypothalamus. For electrical stimulation, the system includes an electrical stimulation lead adapted for implantation on, in, or near the brain stem, and including electrodes adapted to be positioned on, in, or near target nerve tissue in the brain stem, for delivering electrical stimulation energy to the target nerve tissue. For chemical stimulation, the system includes an infusion catheter adapted for implantation on, in, or near the brain stem, and including openings adapted to be positioned on, in, or near target nerve tissue in the brain stem, for delivering a chemical to the target nerve tissue. The system also includes a stimulation source adapted for implantation in the person's body and operable to generate pulses of electrical stimulation energy or pulses of the chemical, for delivery to the target nerve tissue in the brain stem.

A predetermined brain region can be indirectly stimulated by implanting a stimulation lead in communication with a cranial nerve (e.g. olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and the hypoglossal nerve) as well as high cervical nerves (cervical nerves have anastomoses with lower cranial nerves) such that stimulation of a cranial nerve indirectly stimulates the predetermined brain region. Such techniques are further described in U.S. Pat. No. 7,734,340, U.S. Pat. Nos. 6,721,603; 6,622,047; and 5,335,657, and U.S. Provisional Application 60/591,195 entitled "Stimulation System and Method for Treating a Neurological Disorder" each of which are incorporated herein by reference.

Peripheral Nervous System Stimulation

Mechanisms of red cell death could also be inhibited. In an embodiment, electrical stimulation is used to alter autonomic tone of blood vessels that perfuse the bone marrow where erythrocytes are formed to promote larger red cells that would have greater hemoglobin-carrying capacity and longer lifetime.

Peripheral vasodilation may also be used to change systemic oxygen demand for hypoxic stimulation of erythropoietin production.

A neurological lead may be implanted adjacent to one or more nerves of the peripheral nervous system of the patient. In an embodiment, systemic oxygen demand is changed to affect hypoxic stimulation of erythropoietin production by causing peripheral vasodilation and renal vasoconstriction.

Determining Autonomic Tone

In certain embodiments, autonomic tone is measured in order to determine a treatment strategy and/or to provide feedback as to the effectiveness of the treatment strategy. Stimulation of EPO through the sympathetic nervous system, as described above; may not be appropriate under certain circumstances where a patient's anemia is found to be caused by vagal withdrawal, rather than an inability to create EPO. In certain embodiments, neurostimulation to invoke autonomic balance is performed prior to, or in lieu of sympathetic EPO stimulation. In certain embodiments, autonomic tone is monitored in order to provide feedback to a neuromodulation device for treatment of anemia.

U.S. Pat. No. 7,711,415, incorporated herein by reference in its entirety, describes exemplary implantable devices capable of independently monitoring sympathetic and parasympathetic influences on the heart. This can be accomplished, for example, by using one or more processors to assess the level of parasympathetic tone in one of the following manners: determining the patient's diurnal variation of cardiac intervals based on the measured cardiac intervals, and assessing the level of parasympathetic tone based on the diurnal variation of cardiac intervals; determining the patient's diurnal variation of heart rate based on the measured cardiac intervals, and assessing the level of parasympathetic tone based on the diurnal variation of heart rate; and identifying each said cardiac interval that is longer than the immediately preceding cardiac interval as being indicative of cardiac deceleration, and assessing the level of parasympathetic tone based on the cardiac intervals that are identified as being indicative of cardiac deceleration.

The one or more processor may assess the level of sympathetic tone in one of the following manners: by determining the patient's average cardiac interval based on the measured cardiac intervals, and assessing the level of sympathetic tone based on the determined average cardiac interval; by determining the patient's average heart rate based on the measured cardiac intervals, and assessing the level of sympathetic tone based on the determined average heart rate; and by identifying each said cardiac interval that is shorter than the immediately preceding cardiac interval as being indicative of cardiac acceleration, and assessing the level of sympathetic tone based on the cardiac intervals that are identified as being indicative of cardiac acceleration.

Autonomic tone of the patient can also be monitored using photo-plethysmography (PPG), as described in U.S. Pat. No. 7,177,686, entitled "Using Photo-Plethysmography to Monitor Autonomic Tone and Performing Pacing Optimization based on Monitored Autonomic Tone," filed Jan. 23, 2004, which is incorporated herein by reference in its entirety. This can be accomplished, for example, by incorporating a light source and light detector into the same implantable stimulation device that is used for pacing, as is described in detail in the application just incorporated by reference, as well as in U.S. Pat. Nos. 6,591,639 and 6,40,675, which are also incorporated herein by reference in their entirety. Changes in autonomic tone then can be monitored based on changes in pulse amplitude associated with a PPG signal that is produced using the light source and light detector. For example, this can include: recognizing an increase in pulse amplitude as a decrease in the sympathetic tone of the patient; recognizing an increase in pulse amplitude variability as a decrease in the sympathetic tone of the patient; recognizing a decrease in pulse amplitude as an increase in the sympathetic tone of the patient; and/or recognizing a decrease in pulse amplitude variability as an increase in the sympathetic tone of the patient. This may also include: recognizing an increase in pulse amplitude as an increase in the parasympathetic tone of the patient; recognizing an increase in pulse amplitude variability as an increase in the parasympathetic tone of the patient; recognizing a decrease in pulse amplitude as a decrease in the parasympathetic tone of the patient; and/or recognizing a decrease in pulse amplitude variability as a decrease in the parasympathetic tone of the patient. Various thresholds can be defined to distinguish between the different levels of autonomic tone, which can include extremely sympathetic, predominantly sympathetic, neutral, predominately parasympathetic and extremely parasympathetic.

Parasympathetic (i.e., vagal) activity is the major contributor to the high-frequency (HF, 0.15-0.4 Hz) components of HRV, while both vagal and sympathetic activities contribute to its low-frequency (LF, 0.04-0.15 Hz) components. Thus the power of HRV in the HF band has widely been used to quantitatively describe vagal activity and the ratio of LF to HF spectral powers have been utilized as a broad index of "sympathovagal balance".

Other schemes for monitoring autonomic tone, e.g., via the well-known technique of heart rate variability, are also within the spirit and scope of the present disclosure. In such techniques, a measure of sympathovagal balance is often given in terms of some form of standard deviation in RR intervals (e.g., SDNN, a time domain approach) or ratio of low to high frequency components of the power spectrum (the spectral approach).

More specifically, in one time domain approach, the standard deviation of RR intervals (SDNN) is measured. In this approach, an increase in SDNN is interpreted as an increased predominance of the sympathetic component (and a proportional decrease in the parasympathetic component), where a decrease in the SDNN is interpreted as an increased predominance of the parasympathetic component (and a proportional decrease in the parasympathetic component).

In one spectral approach, measures of normal RR intervals are converted into the frequency-domain so that its spectral frequency components can be analyzed. Two frequency bands are indicated as being of interest, including, e.g., a low frequency (LF) band (e.g., between 0.04 Hz and 0.14 Hz) and a high frequency (HF) band (e.g., between 0.15 Hz. and 0.40 Hz). The HF band of the R-R interval signal is believed to be is influenced by only the parasympathetic component of the autonomic nervous system. The LF band of the R-R interval signal is believed to be influenced by both the sympathetic and parasympathetic components of the autonomic nervous system, Consequently, the ratio LF/HF is used as an indication of the autonomic balance between sympathetic and parasympathetic components of the autonomic nervous system. More specifically, an increase in the LF/HF ratio is interpreted as an increased predominance of the sympathetic component (and a proportional decrease in the parasympathetic component), where a decrease in the LF/HF ratio is interpreted as an increased predominance of the parasympathetic component (and a proportional decrease in the parasympathetic component).

A related time domain approach obtains a first measure that is believed to be influenced by only the parasympathetic component of the autonomic nervous system, and a second measure that is believed to be influenced by both the sympathetic and parasympathetic components of the autonomic nervous system. As in the above described spectral approach, a ratio is then taken of the two measures to obtain a measure of the autonomic balance between sympathetic and parasympathetic components of the autonomic nervous system. Similarly, an increase in the ratio is interpreted as an increased predominance of the sympathetic component (and a proportional decrease in the parasympathetic component), where a decrease in the ratio is interpreted as an increased predominance of the parasympathetic component (and a proportional decrease in the parasympathetic component).

Sympathetic activity may also be detected using microneurography (efferent post-ganglionic muscle sympathetic nerve activity, MSNA) and regional norepinephrine spillover technique. In microneurography, a solid tungsten microelectrode or a concentric electrode with an outer diameter of only 200 micrometers is inserted percutaneously and positioned intraneurally. The very small surface of the active recording electrode is brought in intimate contact with nerve fibers within an individual nerve fascicle, while the reference electrode surface is positioned nearby, thereby permitting the recording of an electroneurogram of electrically induced nerve responses derived from the entire nerve fiber spectrum, i.e. from both thick and thin myelinated fibers and from thin, unmyelinated fibers, having diameters between 20-1 micrometers and conduction velocities between 70-1 msec. MSNA measurements are described in Tulppo M P et al. Physiological background of the loss of fractal heart rate dynamics. Circulation, July 19; 112(3):314-9, 2005, incorporated herein by reference.

Blood pressure variability (BPV) and baroreflex function (baroreceptor sensitivity, BRS) may also be measured in accordance with well-known procedures in the art and used to assess autonomic balance. BRS indices correlate negatively with BPV and positively with HRV.

Complex demodulation (CDM) is a method for analyzing heart rate and reveals instantaneous dynamic changes in heart rate and blood pressure that are not revealed by the standard spectral methods. COM is discussed in Shin et al., "Assessment of autonomic regulation of heart rate variability by the method of complex demodulation," IEEE Transactions on Biomedical Engineering, vol. 36, No. 2, February 1989, which is incorporated herein by reference.

Neurostimulation to Maintain Sympathetic/Parasympathetic Balance

In an embodiment a neuromodulation system is used in patients demonstrating severe autonomic failure for maintenance of sympathetic balance, which would secondarily maintain the expected compensatory erythropoietin response. U.S. Pat. No. 6,937,896 ("Kroll"), incorporated herein by reference in its entirety, describes methods and systems for stimulating the intrinsic nervous system of the heart to allow for maintenance of sympathetic balance. In certain embodiments, the Kroll system is modified to provide for maintenance of the expected compensatory erythropoietin response. Heart rate variability based continuous detection of the underlying sympathetic and parasympathetic system and balance thereof will be used as a closed loop system to detect and then stimulate to provide autonomic balance. Systemic inflammation may be alleviated by restoring autonomic balance, which may secondarily relieve the patient's anemia.

Parasympathetic activity may be increased to restore autonomic balance by electrically stimulating the fibers of the cranial nerve X, known as vagus nerve, transvenously by means of an endovascular electrode implanted in, for example, the superior vena cava. U.S. Pat. Nos. 7,813,805 and 8,473,068, incorporated herein by reference in its entirety, describe subcardiac threshold vagal nerves stimulation apparatuses suitable for use in certain embodiments. US Publication No. 2010/0114227, incorporated herein by reference in its entirety, vagal nerves stimulation apparatuses suitable for use in certain embodiments.

Sympathetic Deficiency

In certain embodiments, for patients demonstrating a deficiency in the sympathetic nervous system, stimulation of the renal nerves can be used to increase EPO production.

Determining State of Inflammation

In certain embodiments, the level of systemic inflammation of the patient is measured in order to determine a treatment strategy. The state of inflammation is also a marker of autonomic imbalance. In certain embodiments, the patient may benefit from a systemic decrease in inflammation prior to, or instead of, stimulation of sympathetic stimulation to produce EPO. In certain embodiments, the level of systemic inflammation of the patient is monitored in order to provide feedback to a neuromodulation device.

In certain embodiments, the patient's state of inflammation is assessed using a blood sample. The concentration of inflammatory and anti-inflammatory cytokines can be assessed. IL-6 has been shown to causes a build-up of the glycoprotein, fibrogen in the blood, which thickens the blood. The level of fibrogen can also be determined.

In certain embodiments, a patient's state of inflammation can be determined using a compound action potential (CAP) of a nerve. Such a CAP may be an intrinsic response or an evoked CAP (ECAP). There is an inverse relationship between CAP and the level of inflammation, such that a decrease in CAP indicates an increase in the inflammatory state of the patient. Inflammation causes the nerve's action potential to record slower conduction.

A compound action potential (CAP) is a signal recorded from a nerve trunk made up of numerous axons. It is the result of summation of many action potentials from the individual axons in the nerve trunk. U.S. Pat. No. 7,634,315, which is incorporated herein by reference in its entirety, describes systems and methods for acquiring a nerve's CAP that may be used to assess a patient's inflammatory state according to certain embodiments.

Figure 6A:
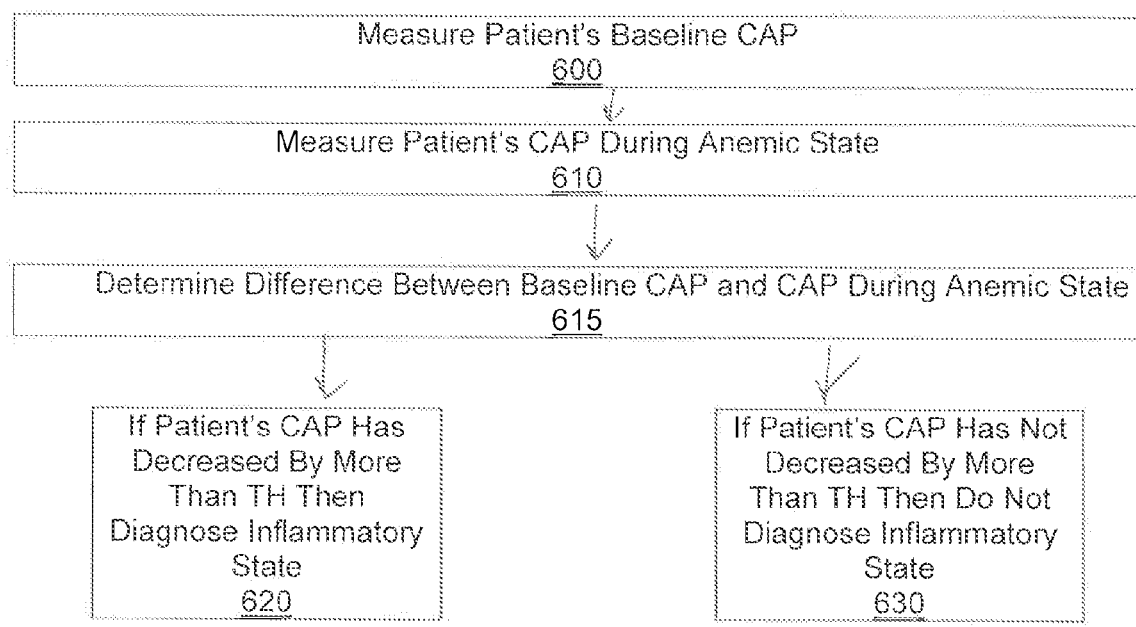
FIG. 6A is a simplified flowchart of an embodiment for determining a patient's inflammatory state according to certain embodiments.
Figure 6B:
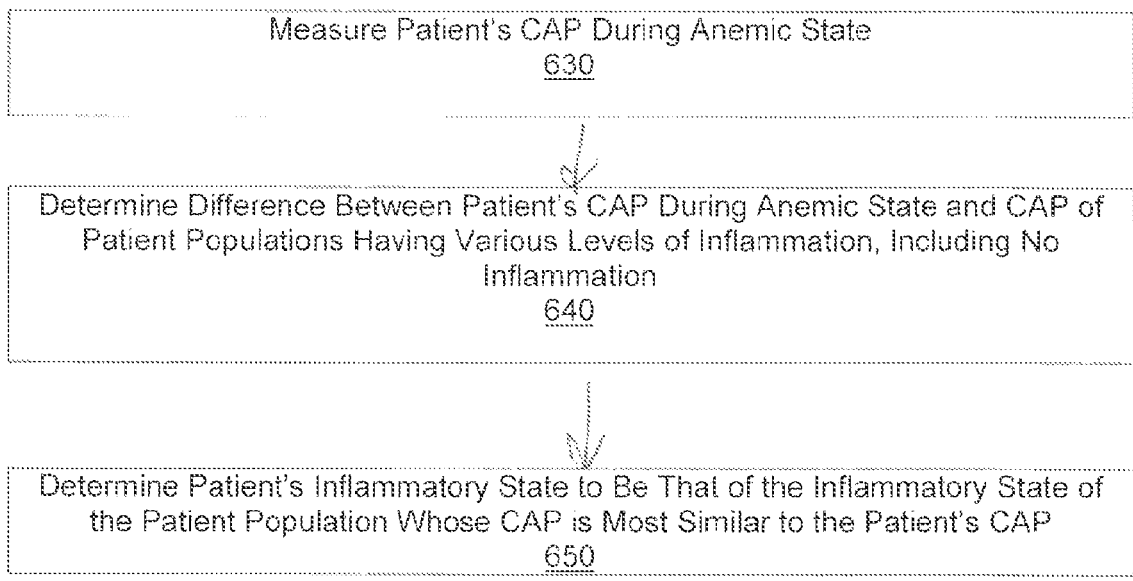
FIG. 6B is a simplified flowchart of an embodiment for determining a patient's inflammatory state according to certain embodiments.

FIGS. 6A-6B illustrates a method for determining a patient's state of inflammation that can be used during the diagnostic stage to determine appropriate therapy and/or as feedback for a closed loop system during treatment. In the illustrated embodiment, a compound action potential (CAP) of a nerve trunk is used to detect a patient's level of inflammation. In an embodiment illustrated in FIG. 6A, a patient's baseline CAP is measured prior to the onset of an anemic state and/or when the patient is otherwise healthy 600 and during an anemic state 610, and the measurements are compared 615. If the patient's CAP has decreased above a threshold, then an inflammatory state is diagnosed 620. If the patient's CAP has not decreased above a threshold, then an inflammatory state is not diagnosed 630. In an embodiment illustrated in FIG. 6B, CAP values determined for patient populations are used instead of the patient's baseline. A patient's CAP is determined during an anemic state 630. An algorithm or look-up table can be used to compare the patient's CAP with a CAP of patients who are not in an inflammatory state, as well as with patients having various levels of inflammation 640. The patient's inflammatory state can then be determined to be that of the inflammatory state of the patient population whose CAP is most similar to that of the patient's. If the patient is determined to be in an inflammatory state, the system may first act to alleviate systemic inflammation, as described in further detail below, prior to or in lieu of sympathetic stimulation of EPO production.

Neurostimulation to Decrease Inflammation and Increase Hemoglobin Production

In an embodiment, vagal nerve stimulation is used to inhibit the production of pro-inflammatory cytokines that may either be initiated in response to the production of EPO resulting from hypoxic conditions or otherwise, and upregulate the production of NO.

Vagal nerve stimulation may be used to inhibit release of pro-inflammatory cytokines. U.S. Pat. No. 7,869,869, filed Jan. 11, 2006, entitled "Subcardiac Threshold Vagal Nerve Stimulation" and U.S. patent application Ser. No. 11/283,229, filed Nov. 18, 2005, entitled "Endovascular Lead System for Chronic Nerve Stimulation," now abandoned, are each incorporated herein by reference in their entirety, can be modified in accordance with certain to reduce inflammation disrupting a patient's hemoglobin production. The neural tract of the vagus nerve that modulates immune response functions at a lower firing threshold than cardioinhibitory fibers. Cholinergic anti-inflammatory pathway regulates TNF production in discrete macrophage populations via two serially connected neurons: one preganglionic, originating in the dorsal motor nucleus of the vagus nerve (or posterior motor nucleus of vagus), which is a cranial nerve nucleus for the vagus nerve in the medulla that lies under the floor of the fourth ventricle; the second postganglionic, originating in the celiac-superior mesenteric plexus and projecting in the splenic nerve. According to certain embodiments, one or both of these pathways are stimulated in order to reduce inflammation.

In certain embodiments, the afferent vagus nerve is also blocked in order to avoid stimulation of other organs upstream of the celiac-superior mesenteric plexus ganglion. In certain embodiments, the renal nerve is blocked in order to avoid an increase in blood pressure and/or an exacerbation of proinflammatory cytokine overproduction. In certain embodiments, the renal nerve is denervated in order to avoid an increase in blood pressure and/or an exacerbation of proinflammatory cytokine overproduction and/or avoid other consequences of an overstimulated RAS. Renal denervation may be accomplished through, e.g., an intravascular radiofrequency ablation catheter. U.S. Publication Nos. U.S. Publication Nos. 2013/0289650, 20130218029, 20130085489, 20130282000, 20130245621, 20130090637, 20110118726, and 20110137298, each of which is incorporated herein by reference in its entirety, provides an example of a suitable apparatus that may be used to denervate the renal sympathetic nerves.

In certain embodiments, the cervical vagus is stimulated. In certain embodiments, one or both common celiac branches of the vagus nerve are stimulated.

Experimental studies in animal models suggest that SCS at lumbar spinal segments (L2-L3) produces vasodilation in the lower limbs and feet which is mediated by antidromic activation of sensory fibers and release of vasoactive substances, and decreased sympathetic outflow. In certain embodiments, the spinal cord is stimulated at L2-L3 to decrease sympathetic overdrive.

Determination of EPO Stimulation Associated Inflammation

Figure 7:
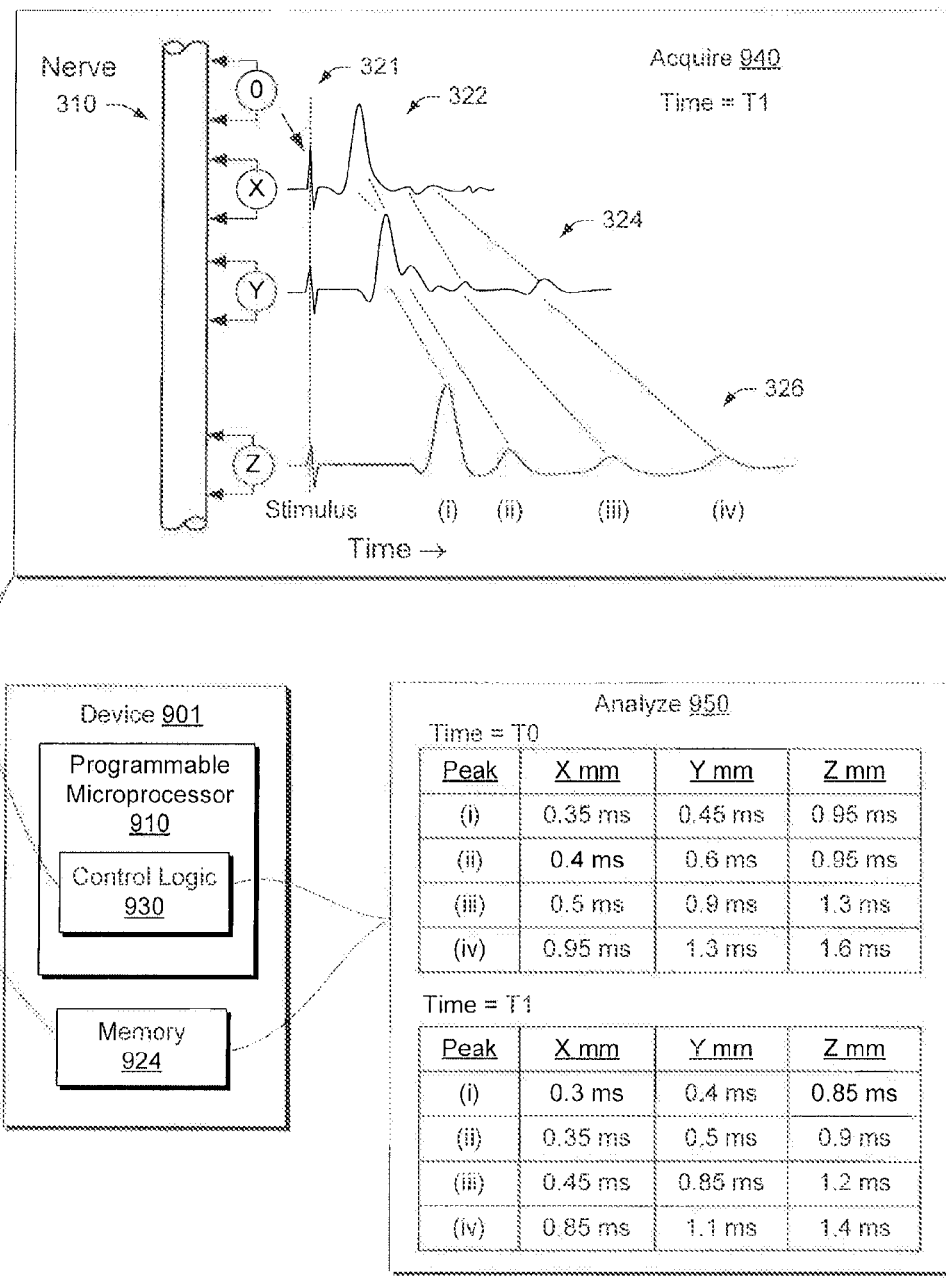
FIG. 7 is a block diagram of an exemplary method for acquisition of compound action potentials and analysis of such potentials.

In an embodiment illustrated in FIG. 7, specificity of the EPO stimulation associated inflammation is determined using CAP. This information can be used in a closed loop system to optimize programmed parameters and to prevent EPO stimulation from exacerbating the patient's state of inflammation.

FIG. 7 shows an exemplary method 900 that includes acquiring CAP information 940 and analyzing ECAP information 950. The method 900 is illustrated in conjunction with an exemplary device 901, which may be an implantable device or a device in communication with an implantable device, and in conjunction with ECAP information. The device 901 includes a programmable microprocessor 910, control logic 930 and memory 924. The control logic 930 may be in the form of instructions stored on a digital data storage medium accessible by the processor 910 where the instructions cause the processor to perform various actions. The device 901 may include any of the various features of the device 100 of FIG. 1, the programmer 1330 of FIG. 11 or the computing device 1340 of FIG. 11.

The acquisition block 940 includes acquiring a series of ECAPs, which may include sampling an entire ECAP, a portion of an ECAP or one or more characteristics of an ECAP. More specifically, ECAPs are acquired from one or more sites along a nerve responsive to delivery of energy. The site of energy delivery may be the same for all of the acquired ECAPs and the ECAPs may be responsive to the same stimulus. For example, in FIG. 7, site "0" represents a site for delivery of energy while sites "X", "Y" and "Z" represent other sites where ECAPs may be acquired. Distances between site 0 and sites X, Y and Z may be known (e.g., X mm, Y mm and Z mm) and used for analyzing acquired ECAP information. Latency (e.g., time between site 0 and another site) may be used as a relative indication of nerve demyelination and/or other nerve condition.

An exemplary method may delivery energy at site 0 and then acquire ECAP information at one or more sites or an exemplary method may delivery energy at site 0 and then acquire ECAP information at one site, deliver energy at site 0 and then acquire ECAP information at another site, etc. While this latter example uses one energy delivery site and multiple acquisition sites, another example may use one acquisition site and multiple energy delivery sites. Thus, depending on delivery and acquisition technique, a method may acquire ECAP information for overlapping segments of a nerve and/or separate segments of a nerve.

The acquisition block 940 indicates an acquisition time of T1 (time when EPO stimulation was engaged). The analysis block 920 shows ECAP information for time T1 along with ECAP information for time T0 (e.g., time when EPO stimulation is engaged), which represents a time earlier than T1. More specifically, in the example of FIG. 7, the ECAP information includes latencies for conduction from site 0 to sites X, Y and Z. Further, various peaks have been identified and a latency is given for each peak, where possible, for example, depending on acquisition and/or analysis techniques (noting that peaks may overlap for one site yet be distinct for another site). The ECAP information of the analysis block 950 may be used to assess nerve condition and may optionally be used to assess nerve condition with respect to nerve fiber type (e.g., where the peaks correspond to different fiber types). Hence, state of inflammation may be specific to a particular type or types of nerve fiber. The stimulation will be conducted at an amplitude that ensures the capture of a population of neurons.

Figure 8:
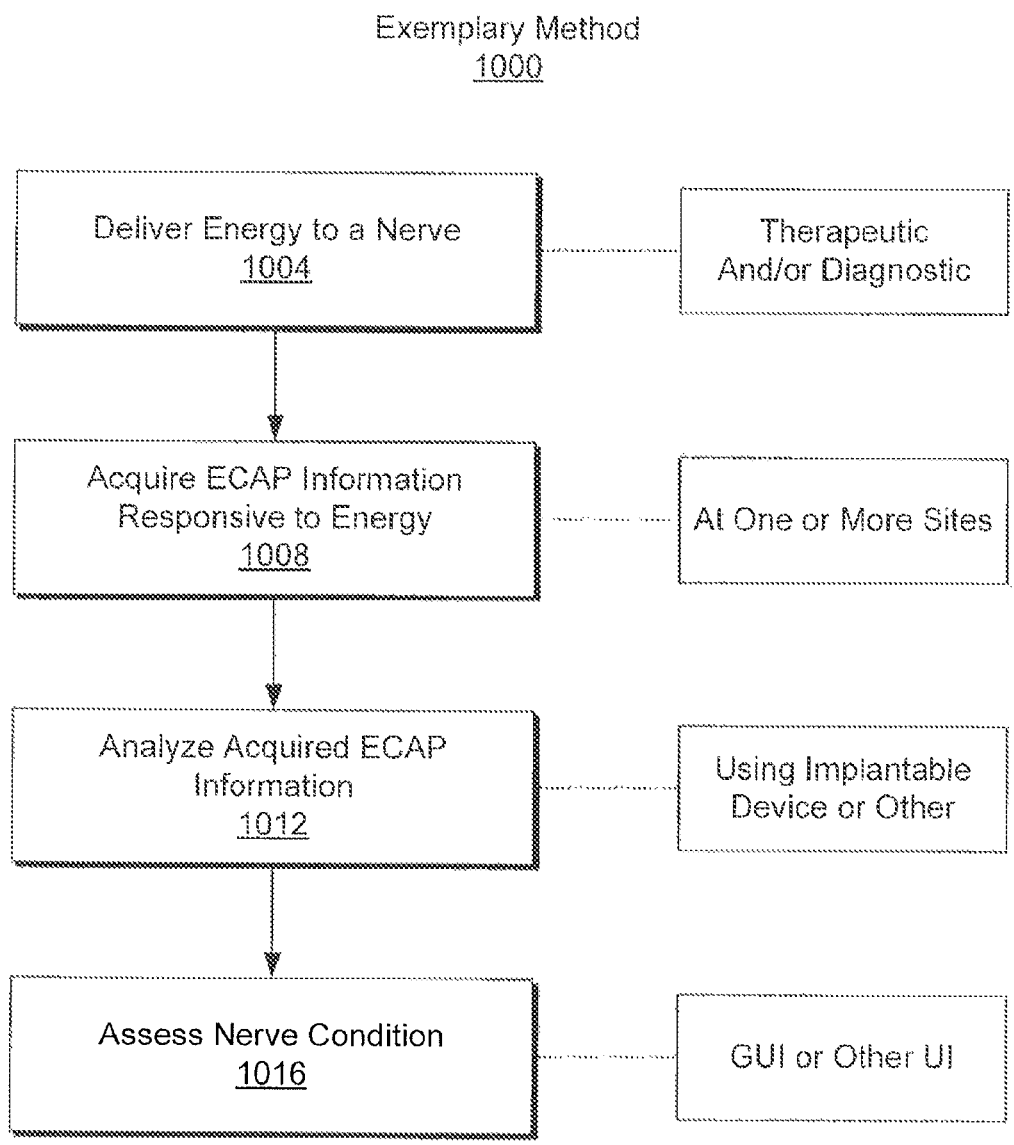
FIG. 8 is a block diagram of an exemplary method for acquisition of compound action potentials and analysis of such potentials.

FIG. 8 shows an exemplary method 1000 for assessing EPO stimulation specific inflammation. The method 1000 commences in a delivery block 1004 that delivers energy to a nerve. The energy may be therapeutic energy associated with stimulation of EPO production or diagnostic energy for the purpose of diagnosing the state of inflammation. An acquisition block 1008 acquires ECAP information responsive to the delivered energy. The acquisition may occur at one or more sites (see, e.g., the example of FIG. 7).

Figure 11:
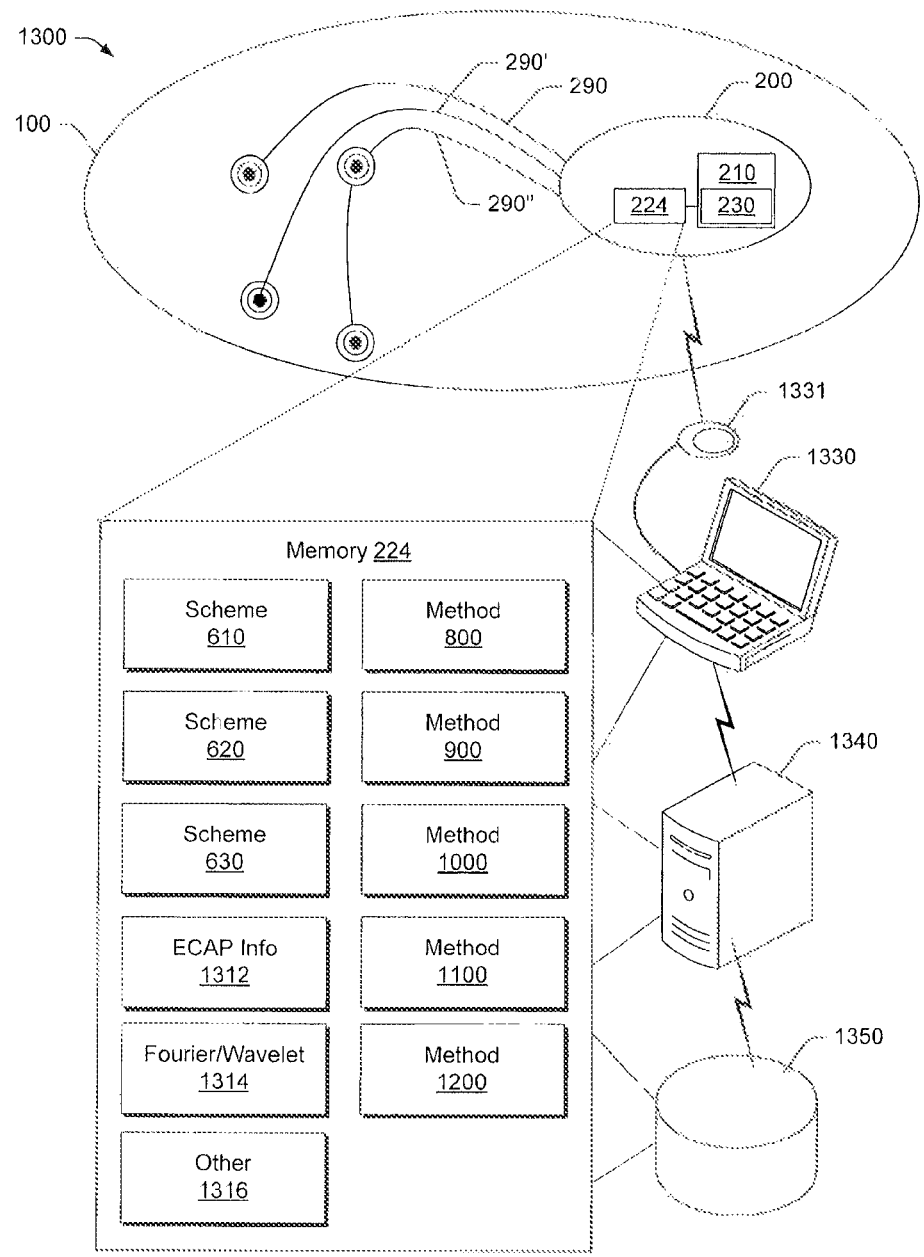
FIG. 11 is a diagram of an exemplary system that includes an implantable device for acquiring compound action potentials and various external devices that may analyze such potentials and/or provide for assessment of inflammation caused by electrical stimulation of a nerve according to certain embodiments.

An analysis block 1012 analyzes the acquired ECAP information, optionally in conjunction with previously acquired or analyzed ECAP information. Such an analysis may occur using an implantable device and/or an external device. For example, FIG. 11 shows an implantable device 200 in communication with an external device 1330. In this example, analyzing may occur solely on the implantable device 200, solely on the external device 1330 or on a combination of the implantable device 200 and the external device 1330.

An assessment block 1016 presents information to a clinician using analyzed ECAP information. The information may be presented in the form of a graph, a table, an alert (buzzer, phone message, etc.) or other user interface. A clinician may optionally adjust one or more operational parameters of a therapeutic and/or a diagnostic process based at least in part on such presented information. For example, the device 1330 may be capable of programming the implantable device 100 using a graphic user interface that presents nerve assessment information and control buttons, fields, etc. Hence, an exemplary GUI may present nerve assessment information and options for controlling an implantable device on a single GUI or a series of related and linked GUI (e.g., linked via software instructions).

An exemplary method may include implementing a nerve stimulation therapy that includes delivering stimulation energy to a target nerve (e.g., EPO stimulation and/or diagnostic), periodically acquiring compound action potentials responsive to the delivered stimulation energy and assessing the patient's inflammatory state based at least in part on the periodically acquired compound action potentials. Such a method may acquire a compound action potential responsive to every delivery of stimulation energy. Such a method may include renal nerve, carotid sinus nerve, periperhal nerve, and/or splenic nerve, for example, as a target nerve.

Figure 9:
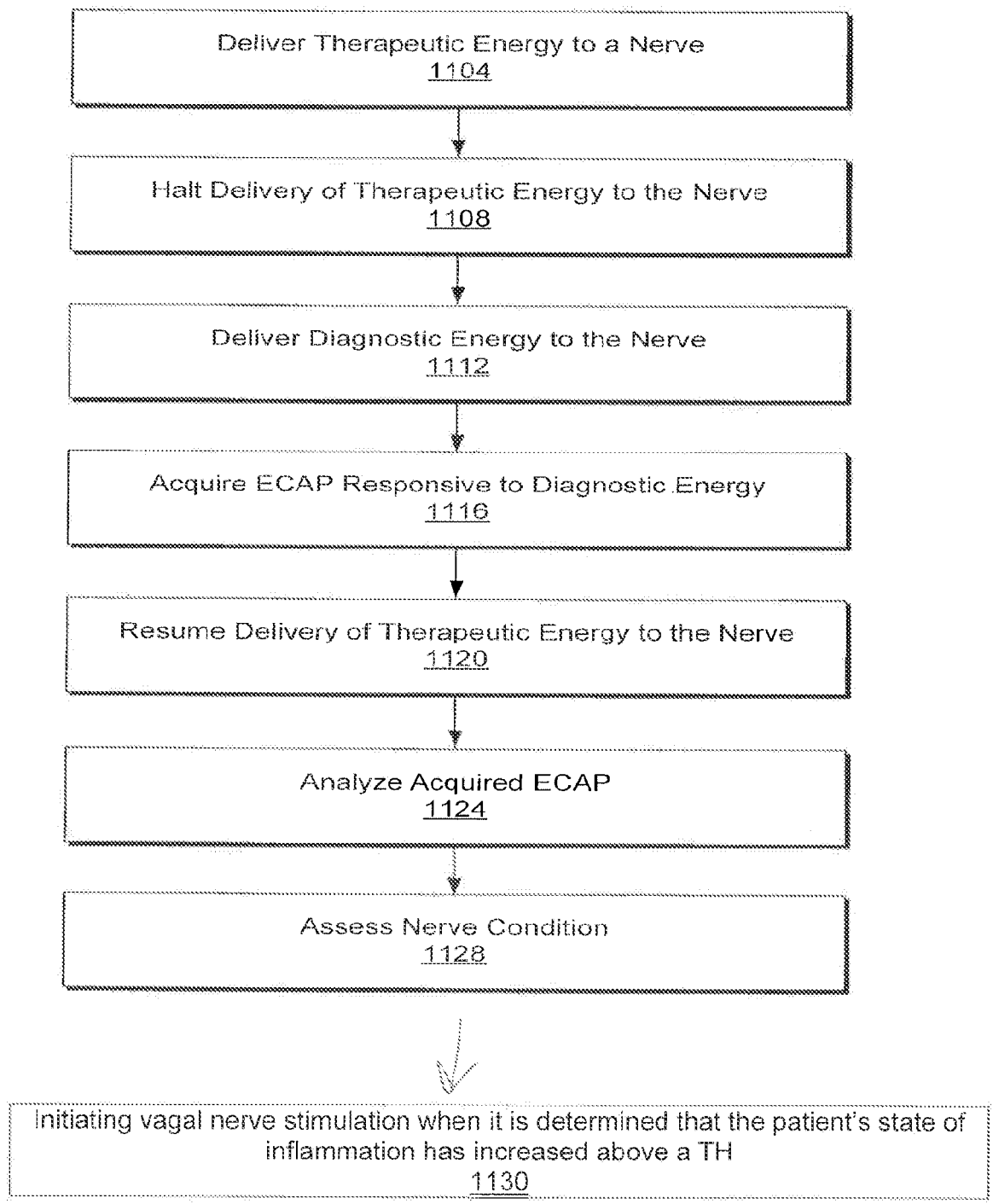
FIG. 9 is a block diagram of an exemplary method for acquisition of compound action potentials and analysis of such potentials.
Figure 10:
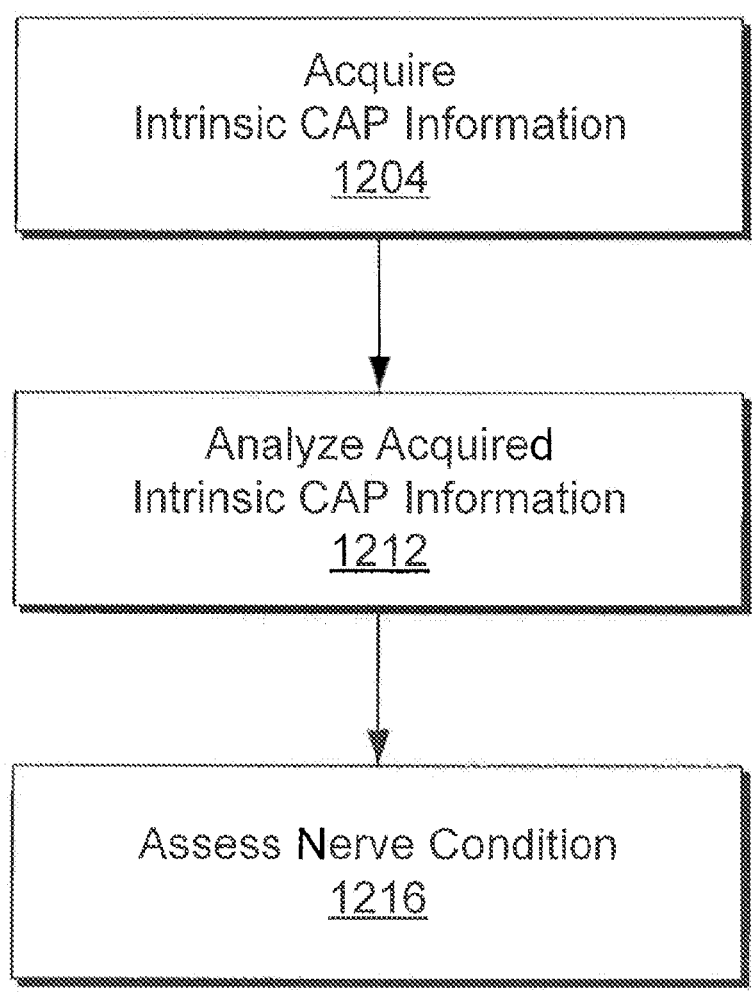
FIG. 10 is a block diagram of an exemplary method for acquisition of intrinsic compound action potentials and analysis of such potentials.

FIG. 9 shows an exemplary method 1100 for assessing the patient's inflammatory condition. The method 1100 commences in a delivery block 1104 that delivers therapeutic energy to a nerve to stimulate EPO production. A subsequent block 1108 halts delivery of the therapeutic energy to the nerve such that another delivery block 1112 can delivery diagnostic energy to the nerve and such that an acquisition block 1116 can acquire ECAP information responsive to the delivered diagnostic energy without interference from the therapeutic energy. Once the diagnostic delivery and ECAP acquisition cycle or loop has occurred, then a block 1120 calls for the delivery of the therapeutic energy to the nerve to resume.

An analysis block 1124 analyzes the acquired ECAP information and an assessment block 1128 may present results of the analysis to a clinician to thereby allow a clinician to assess the patient's state of inflammation caused by EPO stimulation. In an alternative example, an implantable device or external device may assess nerve condition and act accordingly. For example, a device may halt delivery of therapeutic energy to stimulate EPO production and instead begin stimulation of nerve of the inflammatory reflex, such as the vagus nerve. While the various action blocks are shown in a particular order, for example, the blocks 1124 and/or 1128 may occur prior to the block 1120. Hence, in this example, the assessment may control resumption of the therapeutic nerve stimulation.

Neurostimulation of the renal nerves could be used in conjunction with this method in order to result in an overall reduction in inflammation, which could permit effective use of EPO produced, without a counterproductive increase in inflammation.

Anemia in Kidney Failure Patients

In the case of anemia caused by kidney failure, N-acetyl-seryl-aspartyl-lysyl-proline (Ac-SDKP) may be used in conjunction with EPO neurostimulation and/or vagal nerve stimulation. Ac-SDKP is a naturally occurring anti-inflammatory and antifibrotic peptide. Treatment with Ac-SDKP has been shown to reduce inflammation and collagen deposition in the heart, aorta, and kidney in animal models of hypertension, myocardial infarction, and diabetes mellitus. Ac-SDKP has been shown to prevent and reverse renal injury by decreasing inflammatory cell infiltration and renal fibrosis and increasing nephrin protein.

In an embodiment, the sympathetic nervous system in kidneys is blocked to help repair kidneys, either by neuro-hyperpolarization or ablation, to stop inflammatory response but the sympathetic nerves of the carotid arteries are stimulated to indicate hypoxia in conjunction with stimulating the vagal nerve.

Nitric Oxide

Nitric oxide (NO) formed via neuronal nitric oxide synthase (nNOS) in the brain also plays an important role in controlling renal blood flow. Areas of the brainstem with nNOS-containing neurons include the nucleus tractus solitarius, ventrolateral medulla and raphe nuclei. NO from neurons in the brain acts on the paraventricular nucleus of the hypothalamus and the rostral ventrolateral medulla and inhibits the central sympathetic nerve activity to the kidney, leading to renal vasodilatation and increased renal blood flow. In the brain, NO functions mainly as a neuromodulator.

There are also nNOS-containing neurons in sympathetic preganglionic neurons in the spinal cord. Several of the homeostatic actions of spinal afferents are brought about by the release of the transmitters NO and calcitonin gene-related peptide (CGRP) from their peripheral endings.

Brain Stimulation

While some parasympathetic pathways may operate without direct communication to the brain, the brain often activates efferent pathways and receives information via afferent pathways. Thus, the brain includes structures associated with vagal preganglionic neurons.

Activity in the sympathetic nervous system of the spleen may be elicited by stimulation at the hypothalamus as well. In particular, stimulation of the ventromedial nucleus of the hypothalamus is significantly correlated with suppression of natural killer cell cytotoxicity production in the spleen. Such suppression is mediated by β-adrenoreceptors. Splenic nerve fibers terminate in close proximity with lymphocytes expressing β-adrenoreceptors to form a synapse like structure. The stimulation system 100, described above, can be implanted into a person's body with stimulation lead 110 located in communication with a predetermined tissue and/or area of the brain. Such systems that can be used are described in WO2004062470, U.S. Pat. No. 7,734,340, and U.S. Pat. No. 8,239,029 each of which is incorporated herein by reference in its entirety.

The solitary tract nucleus (STN), the main terminal of vagal nerve afferents in the central nervous system, makes anatomic connections with corticotrophin-releasing cells in the paraventricular nucleus of the hypothalamus. Imaging studies have detected activation of the hypothalamus on electrical stimulation of the vagal nerve. In an embodiment, the paraventricular nucleus of the hypothalamus is stimulated in order to decrease inflammation.

Pulse Parameters

According to various exemplary methods and/or devices described herein, a series of pulses, or a pulse train, is typically delivered by an implantable stimulation device to stimulate an autonomic nerve. The pulse train optionally includes pulse parameters or pulse train parameters, such as, but not limited to, frequency, pulse duration (or pulse width), number of pulses, and/or amplitude. These parameters may have broad ranges and vary over time within any given pulse train. In general, a power level for individual pulses and/or pulse trains is determined based on these parameters and/or other parameters. Exemplary ranges for pulse frequency include frequencies ranging from approximately 0.1 to approximately 50 Hz, and, in particular, frequencies ranging from approximately 1 Hz to approximately 7 Hz. It has been found in animal studies that pulse frequencies of below 1 Hz had little to no effect on RBF. Frequencies of between about 1 and about 7 Hz have been found to decrease RBF in a variety of animal models. With frequencies that decreased RBF, there has been shown to be an increase in renin secretion rate and antinatriuresis. Higher frequencies higher than 50 Hz may also be suitable.

Exemplary ranges for pulse duration, or pulse width for an individual pulse (generally within a pulse train), include pulse widths ranging from approximately 0.01 milliseconds to approximately 5 milliseconds and, in particular, pulse widths ranging from approximately 0.1 milliseconds to approximately 1.6 milliseconds. A pulse width of 0.5 ms has been shown to lower RBF in animal models of hypertension. Exemplary pulse amplitudes are typically given in terms of current or voltage; however, a pulse or a pulse trains may also be specified by power, charge and/or energy. For example, in terms of current, exemplary ranges for pulse amplitude include amplitudes ranging from approximately 0.02 mA to approximately 20 mA, in particular, ranging from 0.1 mA to approximately 5 mA. Exemplary ranges for pulse amplitude in terms of voltage include voltages ranging from approximately 2 V to approximately 50 V, in particular, ranging from approximately 4 V to approximately 15 V. 10 V has been used in animal models to achieve a reduction in RBF.

Preconditioning

In an embodiment, the subject's kidneys are preconditioned in order to mitigate any damage to the kidneys during the induced hypoxia. Preconditioning appears to upregulate T-regulatory (Treg) lymphocytes and cell survival pathways, and downregulate apoptotic pathways. Treg cells inhibit neutrophil and macrophage accumulation in the kidney, tubular necrosis and AKI. The preconditioning may begin about two weeks prior to the EPO induction therapy. In certain embodiments, the preconditioning may begin about one week prior to the EPO induction therapy.

Preconditioning may also be used to stimulate correspondent EPO receptor upregulation in the bone marrow.

Plasma EPO levels remain within observed physiologic levels in maintenance dosing regimens, potentially reducing the risk of any off-target effects that could result from abnormally high or supra-physiologic levels of EPO.

In certain embodiments, the levels of time of induced hypoxia are graded, i.e., the cycles of hypoxia induced by neural stimulation are longer and longer, in order to precondition the kidneys from ischemic insult during the EPO induction therapy. In certain embodiments, the preconditioning begins a period of time prior to the EPO induction therapy and the levels of time of induced hypoxia are graded during the preconditioning.

In certain embodiment, remote ischemic preconditioning (rIPC) is used to protect the kidneys prior to the initiation of EPO stimulation therapy. rIPC is a phenomenon whereby short periods of ischemia in one tissue can protect a distant tissue or organ from longer periods of ischemia. Clinical trials have successfully demonstrated that rIPC used to induce transient ischemia in limb muscles attenuated ischemia of the heart and kidneys due to hypoxic conditions during heart surgery. Since rIPC has been demonstrated to attenuate systemic inflammation, rIPC may be used to attenuate the inflammatory response during the EPO stimulation therapy as well. rIPC may involve the release of adenosine, bradykinin, or norepinephrine and activation of $K_{ATP}$ channels.

Oxidative stress may be attenuated by vitamins E and C administration.

Renal stimulation is optimized to achieve a target level of hemoglobin (on a longer time scale), while avoiding any detrimental change in arterial blood pressure (on a shorter time scale).

Feedback

The parameters of the EPO neurostimulation device, whether external or implanted, may be adjusted by monitoring, e.g., serum EPO level, the hematocrit level, hemoglobin concentration, cytokine level, GFR, and renal blood flow. The factors can be used singly or in combination to provide feedback for adjusting EPO stimulation. In a preferred method, hemoglobin is measured, rather than hematocrit levels. Unlike hematocrit, hemoglobin is not significantly affected by shifts in plasma water, as may occur as a consequence of diuretics or with dialysis therapy. Hemoglobin levels are directly affected by lack of erythropoietin production from the kidney and thus serve as a more precise measurement of erythropoiesis.

The target values of the parameters monitored may vary depending on a number of factors, including the subject's disease state, age, physical activity, and gender. In an exemplary embodiment, a female Hodgkin's lymphoma patient's hemoglobin level is monitored and EPO stimulation therapy is only rendered if the subject's hemoglobin level falls below 10.5 g/dL, and then the target hemoglobin level is 10.5 g/dL or greater, but less than about 12 g/dl. In an embodiment, a male Hodgkin's lymphoma patient's hemoglobin level is monitored and EPO stimulation therapy is only rendered if the subject's hemoglobin level falls below 12 g/dL, and then the target hemoglobin level is 12 g/dL or greater, but less than about 13 g/dl.

In certain embodiments, GFR and renal blood flow are measured because they are prompt markers of the effectiveness of neural stimulation.

In certain embodiments, the target level of serum EPO is about 1 to about 500 I.U./kg body weight. In certain embodiments, the target level of serum EPO is about 50 to about 300 I.U./kg body weight. The target level of serum EPO may be adjusted depending on the particular disorder being treated.

In certain embodiments, the hematocrit level after EPO stimulation is monitored. The hemoglobin level is usually about one-third the value of the hematocrit. In certain embodiments, a target range for the hematocrit level for an adult male subjects and postmenopausal women is between about 30% to 37%. In certain embodiments, a target for the hematocrit level for adult male subjects and postmenopausal women is about 36%. In certain embodiments, a target for the hematocrit level for premenopausal women is about 33%.

In an embodiment, it is determined whether a subject is refractory to EPO stimulation, in order to determine whether neurostimulation to promote the production of anti-inflammatory cytokines and/or inhibit the production of inflammatory cytokines should be initiated or escalated.

In an embodiment, serum EPO levels are determined in conjunction with hemoglobin and/or hematocrit levels to determine whether each measurement is within a desired range and to determine a relationship between the measurements.

Whether or not a subject is refractory to EPO stimulation therapy can be assessed by determining the subject's response or predicted response to treatment with EPO stimulation. For example, in an embodiment, the response desired upon treatment with EPO stimulation can be defined as an increase in hemoglobin of at least 2 g/dl over a twelve (12) week period. If a subject does not display such a response within the required period of time, that subject may be deemed refractory to treatment with EPO stimulation.

A target hemoglobin level for an adult female may be 12 g/dL. A target hemoglobin level for an adult female may be 13 g/dL. Therefore, in one embodiment, a subject is determined to be refractory to EPO stimulation therapy if treatment over specific period of time fail to increase hemoglobin to at least 12 g/dL or 13 g/dL, respectively. Treatment of renal anemia to target Hb higher than 13 g/dl has been found to be harmful. Treatment of Hb below 9 g/dl has been found to provide substantial transfusion and quality-of-life benefits, but safety is unknown. After the release of the TREAT study, the recommendations of a Hb level of 10 to 12 g/dl in CKD patients seems adequate. In cancer patients undergoing chemotherapy, some studies have shown that a hemoglobin target level of 12 g/dL or greater resulted in more rapid cancer progression or shortened overall survival in patients with breast, head and neck, lymphoid, cervical, and non-small cell lung malignancies. Other studies have found no statistically significant decrease in overall survival and progression-free survival when the hemoglobin level was targeted at 12.5-13 g/dl.

In certain embodiment, the target Hb levels is 10-12 g/dl. In an embodiment, a cancer patient's hemoglobin level is monitored and EPO stimulation therapy is only rendered if the subject's hemoglobin level falls below 10 g/dL, and then the target hemoglobin level is 10 g/dL or less for the patient's safety. In an embodiment, anti-inflammatory cytokine therapy and or therapy inhibiting the production of pro-inflammatories is rendered in conjunction with the EPO stimulation therapy, and markers for inflammation are monitored, in order to reduce the likelihood that greater EPO levels will be detrimental to the cancer patient.

The normal regulation of erythropoiesis is a feedback loop. Normal plasma EPO levels range from 10 to 30 IU/ml. In an embodiment, optical sensors are used to complete a feedback loop. A device-based diffuse reflectance sensor with two or more wavelengths of infrared and visible light may be used to determine total hemoglobin and/or hematocrit level in the blood. In US Pub. No. 2010/0099964, which is incorporated herein by reference in its entirety, O'Reilly describes a patient monitor system configured to measure and display a hemoglobin concentration measurement suitable for use according to an embodiment of the present invention. According to an embodiment, after a change in EPO stimulation therapy is made, a sensor monitors the hemoglobin level over a typical time course of approximately 7 days to assess the effect of the change.

Hematocrit (Hct) is the percentage of blood volume that is comprised of red blood cells. Chronically implantable optical sensor that can measure and monitor Hct levels are known, as can be appreciated from U.S. Pat. Nos. 7,630,078, 3,847,483 and 4,114,604, each of which is incorporated herein by reference in its entirety. Nabutovsky, in U.S. Pat. No. 7,630,078, discloses implantable systems, and methods for use therewith, that compensate for changes in the intensity of light transmitted by one or more light sources of the implantable systems. The implantable system includes an implantable housing including a window through which light can pass. Included within the housing is at least one light source, a measurement light detector and a calibration light detector. Each light source transmits light of a corresponding wavelength. The intensity of the light transmitted by each light source is controlled by a corresponding drive signal that drives the light source. A portion of the light of each wavelength exits the housing through the window. The measurement light detector detects light of each wavelength scattered back into the housing through the window, and produces a measurement signal that is indicative of the intensity of the light of each wavelength detected by the measurement light detector. The calibration light detector detects a portion of the light of each wavelength that has not exited the housing, to produce a calibration signal that is indicative of the intensity of the light of the wavelength detected by the calibration light detector, which is indicative of the intensity of the light transmitted by each light source. A processor detects changes in the intensity of the light transmitted by each light source based on the calibration signal, and takes such changes in intensity into account by making appropriate adjustments to algorithms that are used to determine levels of hematocrit based on the measurement signal, thereby providing a more accurate detection of the level of hematocrit.

In an embodiment, the Hct sensor is embedded into the implantable system. If there are existing pacing or sensing leads that are part of a cardiac rhythm device, the Hct sensor can be placed on one of the existing leads. The Hct sensor can also be placed on a standalone lead. The Hct sensor could be used either to monitor for the improvement, development, or worsening of anemia. The development of anemia may be marked by a gradual decrease in Hct. A Hot trend could be created from daily or more/less frequent measurements. If a decrease greater than a programmable or set threshold occurs, erythropoietin therapy could be initiated and/or the patient could be notified to contact his physician. Otherwise, he could be prompted to take an extra medication dose, for example an iron supplement.

If there is too much erythropoietin produced, too many red blood cells may be produced, leading to polysythemia, which in turn can lead to an increase in the volume of the blood in circulation, and increase in the blood's viscosity, and lead to hypertension.

Blood Pressure Sensors

An sensor may also be used for estimating blood pressure, as described, e.g., by Fayram in U.S. Pat. No. 8,147,416 and Wenzel in U.S. Pat. No. 8,478,403, each of which is incorporated herein by reference in its entirety, Fayram and Wenzel disclose implantable systems, and methods for use therewith, for monitoring arterial blood pressure on a chronic basis. According to the method described in Fayram, a first signal indicative of electrical activity of a patient's heart, and a second signal indicative of mechanical activity of the patient's heart, are obtained using implanted electrodes and an implanted sensor. By measuring the times between various features of the first signal relative to features of the second signal, values indicative of systolic pressure and diastolic pressure are determined. In specific embodiments, such features are used to determine a peak pulse arrival time (PPAT), which is used to determine the value indicative of systolic pressure. Additionally, a peak-to-peak amplitude at the maximum peak of the second signal, and the value indicative of systolic pressure, are used to determine the value indicative of diastolic pressure.

According to Wenzel, for each of a plurality of periods of time, there is a determination one or more metrics indicative of pulse arrival time (PAT), each of which are indicative of how long it takes for the left ventricle to generate a pressure pulsation that travels from the patient's aorta to a location remote from the patient's aorta. Based on the one or more metrics indicative of PAT, the patient's arterial blood pressure is estimated.

Pressure Sensor

In an embodiment a CardioMEMS-type miniature pressure sensor can be used to monitor cardiac real time performance. The CardioMEMS pressure sensor is a miniature pressure sensor having the size of a small paper pin (i.e., it can be as small as about 0.5 mm.times.2 mm.times.1.5 mm in size), which is made using the MEMS technology. It can be implanted percutaneously via the femoral or the subclavian vein into the patient's right atrium and transseptally into the left atrium. The CardioMEMS pressure sensor can be a wireless sensor. The fixation mechanism can be an opened hoop exerting a pressure against the pulmonary artery (PA), or the sensor can be mounted on a stent-like component which is pressed against the PA inner wall with or without an anchoring mechanism such as that of a transcatheter valve anchoring mechanism. CardioMEMS pressure sensors are developed by CardioMEMS in Atlanta, Ga.

Measuring Blood Oxygen and/or Blood Carbon Dioxide Concentration

Various sensors are known to those having ordinary skill in the art that may be used to measure blood oxygen and/or blood carbon dioxide concentration. Fiber optic $PCO_2$ sensors and $PO_2$ sensors are known that are suitable for blood concentration measurements. One example is a combined Clark-type $PO_2$/Stow-Severinghaus type $PCO_2$ sensor for sensing both $PaO_2$ and $PaCO_2$. Other sensors include gel polymeric electrodes that contain a suitable electrolyte for measuring a selected parameter such as $PCO_2$, $PO_2$, or pH. Various other sensors may be suitable including optical fiber pH sensors, optical fiber $PCO_2$ sensors, thermocouple temperature sensors. Suitable $PO_2$ sensors may be electrochemical $PO_2$ sensors or fluorescent $PO_2$ sensors.

Chronic Use Precautions

FIG. 12 illustrates methods invoking certain precautions in HF patients in order to mitigate exacerbation of the underlying heart disease, and so that the neurostimulation device does not react to acute instability.

In certain embodiments, EPO stimulation is only triggered when the patient's heart rate is within a specific heart rate range 1410. The heart rate tolerance threshold is a programmable value specified by the clinician and may be set, e.g., in the range of 80 bpm-120 bpm. So long as the patient heart rate does not exceed the programmed tolerance threshold, EPO stimulation may be delivered.

In certain embodiments, EPO stimulation is only triggered at night 1420.

In certain embodiments, EPO stimulation is only triggered after it is determined that there is not an acute instability associated with heart failure 1430. The resolution of anemia is a chronic issue and the risks associated with EPO stimulation may fail to outweigh the benefits during periods of acute instability, and other methods of treating the anemia may be more suitable.

U.S. Publication Nos. 2013/0184545 and 2012/0190991, each of which is incorporated herein by reference in its entirety, disclose algorithms used in accordance with certain embodiments to diagnose pulmonary fluid overload within a patient. During a fluid overload situation, the patient may be suffering from a dilution anemia that will be corrected using diuretics and does not require EPO production to resolve the issue. Moreover, the fluid retention associated with congestive heart failure may be caused by sustained reduction in renal blood flow and vasoconstriction. Thus further reduction of renal blood flow may exacerbate the anemia.

EPO stimulation may only be performed when an algorithm determines that the cardiac ischemia is not ongoing 1440. In certain embodiments, an implanted device, e.g., a cardiac rhythm management device, is used to detect myocardial ischemia by evaluating electrogram features to detect an electrocardiographic change. U.S. Pat. No. 8,180,439, U.S. Pat. No. 8,145,309, and U.S. Pat. No. 6,609,023, each of which is incorporated herein by reference in its entirety, describe exemplary implantable devices capable of detecting imminent myocardial infarctions and/or myocardial ischemia that can be used in accordance with certain embodiments. U.S. Publication No. 201310110187, which is incorporated herein by reference in its entirety, describes an implantable ischemia detector configured to detect an ischemic event in the heart if an oxygen sensor signal indicates a temporary decrease in oxygen concentration in the coronary sinus blood below a normal level followed by a temporary increase in oxygen concentration in the coronary sinus blood above the normal level.

In certain embodiments, an implantable device is used to test for heart damage markers or cardiac enzymes in the body fluid. U.S. Pat. No. 8,192,360, incorporated herein by reference in its entirety, discloses an implantable fluid analyzer that can be used in accordance with certain embodiments. In accordance with certain embodiments, creatine kinase (CK) can be used to diagnose or confirm the existence of heart muscle damage. In certain embodiments, CK enzyme, CK-MB can be measured as well. CK-MB shows an increase above normal in a person's blood test about six hours after the start of a heart attack. It reaches its peak level in about 18 hours and returns to normal in 24 to 36 hours. The peak level and the return to normal can be delayed in a person who's had a large heart attack, especially without early and aggressive treatment.

In an embodiment, an implantable device measures the level of other cardiac muscle proteins called troponins, specifically troponin T (cTnT) and troponin I (cTnI). These proteins control the interactions between actin and myosin, which contracts or squeezes the heart muscle. Troponins specific to heart muscle have been found, allowing the development of blood tests (assays) that can detect minor heart muscle injury ("microinfarction") not detected by CK-MB. Normally the level of cTnT and cTnI in the blood is very low. It increases substantially within several hours (on average four to six hours) of muscle damage. It peaks at 10 to 24 hours and can be detected for up to 10 to 14 days.

An algorithm may further be used to determine that whether bleeding is ongoing 1450. If bleeding is ongoing, the patient's baroreflex and blood pressure will be abnormal. Venous return will also be abnormal irrespective of the patient's total peripheral resistance. EPO stimulation will not be initiated during this acute state.

If the algorithm determined that the specific heart rate is achieved, it is a preprogrammed time of day, such as night time, the patient is not suffering from an acute exacerbation of heart failure, no cardiac ischemia or bleeding are ongoing, then the system will trigger EPO stimulation by the neuromodulation device 1460. Anti-inflammatory stimulation, e.g., vagal nerve stimulation may also be triggered simultaneously with EPO production, or at a time when it is determined that EPO production has caused inflammation 1470.

Drug Pump

In further embodiments, it may be desirable to use a drug delivery system independently or in combination with electrical stimulation to result in the stimulation parameters of the present invention or to enhance the effectiveness of the stimulation therapy. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Still further, the present invention can comprise a chemical stimulation system that comprises a system to control release of neurotransmitters (e.g., norepinephrine, epinephrine), chemicals (e.g., zinc, magnesium, lithium) and/or pharmaceuticals that are known to alter the activity of neuronal tissue. For example, infusion formulation delivery system can utilize a control system having an input-response relationship. A sensor generates a sensor signal representative of a system parameter input (such as levels of neurotransmitters), and provides the sensor signal to a controller. The controller receives the sensor signal and generates commands that are communicated to the infusion formulation delivery device. The infusion formulation delivery device then delivers the infusion formulation output to the predetermined site at a determined.

It should be appreciated from the above that the various structures and functions described herein may be incorporated into a variety of apparatuses (e.g., a stimulation device, a lead, a monitoring device, etc.) and implemented in a variety of ways. Different embodiments of such an apparatus may include a variety of hardware and software processing components. In certain embodiments, hardware components such as processors, controllers, state machines, logic, or some combination of these components, may be used to implement the described components or circuits.

In certain embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In certain embodiments some of the connections or couplings represented by the lead lines in the drawings may be in an integrated circuit, on a circuit board or implemented as discrete wires or in other ways.

The signals discussed herein may take various forms. For example, in certain embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in certain embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements.

Closed-Loop System

Referring to FIG. 13, a closed-loop system is used to more safely and efficiently stimulate EPO. In block 1305, the stimulation device 100 monitors the hemoglobin levels of the patient on a continual (e.g., periodic) basis. If anemia is not indicated, the operational flow may proceed back to block 1310 whereby the stimulation device 100 continues to monitor the hemoglobin levels of the patient. In the event anemia is indicated, the operational flow proceeds to block 1315.

At block 1315, the anemia monitor 240 (or some other suitable functional component of the device 100 such as a neuromodulation stimulation controller 239) may select parameters for electrical stimulation based on one or more characteristics of the indicated anemic condition. In some aspects, depending on whether the characterization of the anemic condition indicates anemia, a decision may be made by the anemia monitor 240 to provide stimulation of parasympathetic innervation, sympathetic innervation, or a combination of the two 1320. Here, in an embodiment where the stimulation device 100 is coupled to different stimulation leads (e.g., neurological lead 110) a decision may be made regarding which leads are to be used for the stimulation operation. For example, if autonomic imbalance or an inflammatory state is indicated, the parasympathetic system may be activated (e.g., to balance out an autonomic sympathetic response) and/or the sympathetic system deactivated. In this case, the heart rate of the patient may decrease as a result of the stimulation of one or more parasympathetic nerves. Conversely, if anemia due to sympathetic withdrawal is indicated, the sympathetic system may be activated (e.g., to balance out an autonomic parasympathetic response) and/or the parasympathetic system may be deactivated. In this case, the heart rate of the patient may increase as a result of the stimulation of one or more sympathetic nerves.

In addition, signal parameters such as signal frequency and/or signal amplitude may be selected based on the indicated anemic condition. For example, different parameters may be used for parasympathetic innervation versus sympathetic innervation.

In some implementations the anemia monitor 240 may select one or more of these parameters based on the severity of the anemic condition. For example, if the anemic condition is not severe, a relatively small signal magnitude and/or a relatively low frequency may be selected for the stimulation operation. Conversely, if the anemic condition is relatively severe, a relatively large signal magnitude and/or a relatively high frequency may be selected for the stimulation operation.

Also, in some aspects the length of time that a stimulation signal is to be applied may be based on the anemic condition. For example, the anemia monitor 310 may designate stimulation duration times based on whether anemia is indicated and/or based on the severity of the anemic condition.

As represented by block 1330, the stimulation device 100 may then generate one or more stimulation signals to stimulate the patient's nervous system. To this end, the stimulation device 100 may include a neurostimulation signal generator 312 (e.g., comprising a pulse generator) that is coupled to at least one nerve stimulation lead (e.g., neurological lead 104). Here, the at least one nerve stimulation lead may be implanted to stimulate one or more parasympathetic nerves and/or implanted to stimulate one or more sympathetic nerves. In some implementations, the neurosignal generator 238 may be configured to generate a bi-polar square wave or some other waveform suitable for nerve stimulation.

As represented by block 1335, during and/or after stimulation of the nervous system, the stimulation device 100 may monitor cardiac activity (e.g., by processing acquired IEGM data) to determine the effect of the stimulation on the patient's condition and adapt the stimulation accordingly. In certain embodiments, impedance sensors are used to determine the stroke volume, cardiac output to monitor the cardiac status to ensure no sludge formation and ensure systemic integrity. Impedance sensors for alignment of RBCs (cells are aligned: impedance is low)—check integrity of blood quality at the level of the heart (endocardial blood volume). In particular, the impedance of high frequency current driven in parallel to the aorta, for example from the chest to the abdomen, should have larger decreases during systole versus that measured during diastole, indicating a higher hematocrit overall (high impedance during diastole because of many RBCs randomly distributed, disturbing the electric field in the great vessels) and better overall flow (low impedance during systole because of the high degree of parallel alignment of RBCs in the ascending and descending aorta allowing current to flow freely).

U.S. Publication No. 2012/0239104 ("Rosenberg"), incorporated herein by reference in its entirety, describes a method that can be used according to an embodiment to measure cardiogenic impedance from one or more vectors, preferably multiple vectors, to measure cardiac integrity that can be used to determine whether EPO therapy should be triggered and/or for feedback in a closed loop system. Rosenberg provides a method for measuring cardiogenic impedance (CI) along at least a first vector to determine stroke volume, venous return, cardiac contractility status, and ejection times.

Changes in contractility also produce significant changes in ejection fraction (EF). Increasing contractility leads to an increase in EF, while decreasing contractility decreases EF. Therefore, EF is often used as a clinical index for evaluating the inotropic state of the heart. In heart failure, for example, an associated decrease in contractility leads to a fall in stroke volume as well as an increase in preload, thereby decreasing EF. The increased preload, if it results in a left ventricular end-diastolic pressure greater than approximately 20 mmHg, can lead to pulmonary congestion and edema. Treatment of a patient in heart failure with an inotropic drug (e.g., beta-adrenoceptor agonist or digoxin) shifts the depressed Frank-Starling curve up and to the left, thereby increasing stroke volume, decreasing preload, and increasing EF.

For example, as represented by block 1318, the stimulation may be modified if the severity of the anemic condition has changed, if the patient's heart rate has changed, if there has been a change in the quantity or severity of observed PVCs, if there has been a change in cardiac integrity, and so on. In the even that EPO stimulation causes an imbalance of the autonomic nervous system, as indicated by a detriment to cardiac integrity, the parameters of stimulation of the nerves may be altered, as disclosed in, e.g., U.S. Pat. No. 6,937,896, discussed above, to improve cardiac integrity.

As a specific example, if the stimulation has mitigated the severity of the response to the anemic condition, the amplitude and/or the frequency of the stimulation signal may be decreased. Similarly, if anemia is no longer indicated, the application of stimulation may be terminated, as represented by block 1320. In any event, the stimulation device 100 may continue to monitor the patient's condition over time and apply an appropriate level of neurostimulation whenever it is warranted.

As mentioned above, in some implementations the teaching herein may be implemented in an implantable cardiac device that is used to monitor and/or or treat cardiac various conditions. The following description sets forth an exemplary implantable cardiac device (e.g., a stimulation device such as an implantable cardioverter defibrillator, a pacemaker, etc.) that is capable of being used in connection with the various embodiments that are described herein. It is to be appreciated and understood that other devices, including those that are not necessarily implantable, can be used and that the description below is given, in its specific context, to assist the reader in understanding, with more clarity, the embodiments described herein.

Transcutaneous Neuromodulation for Treatment of Anemia

Figure 14:
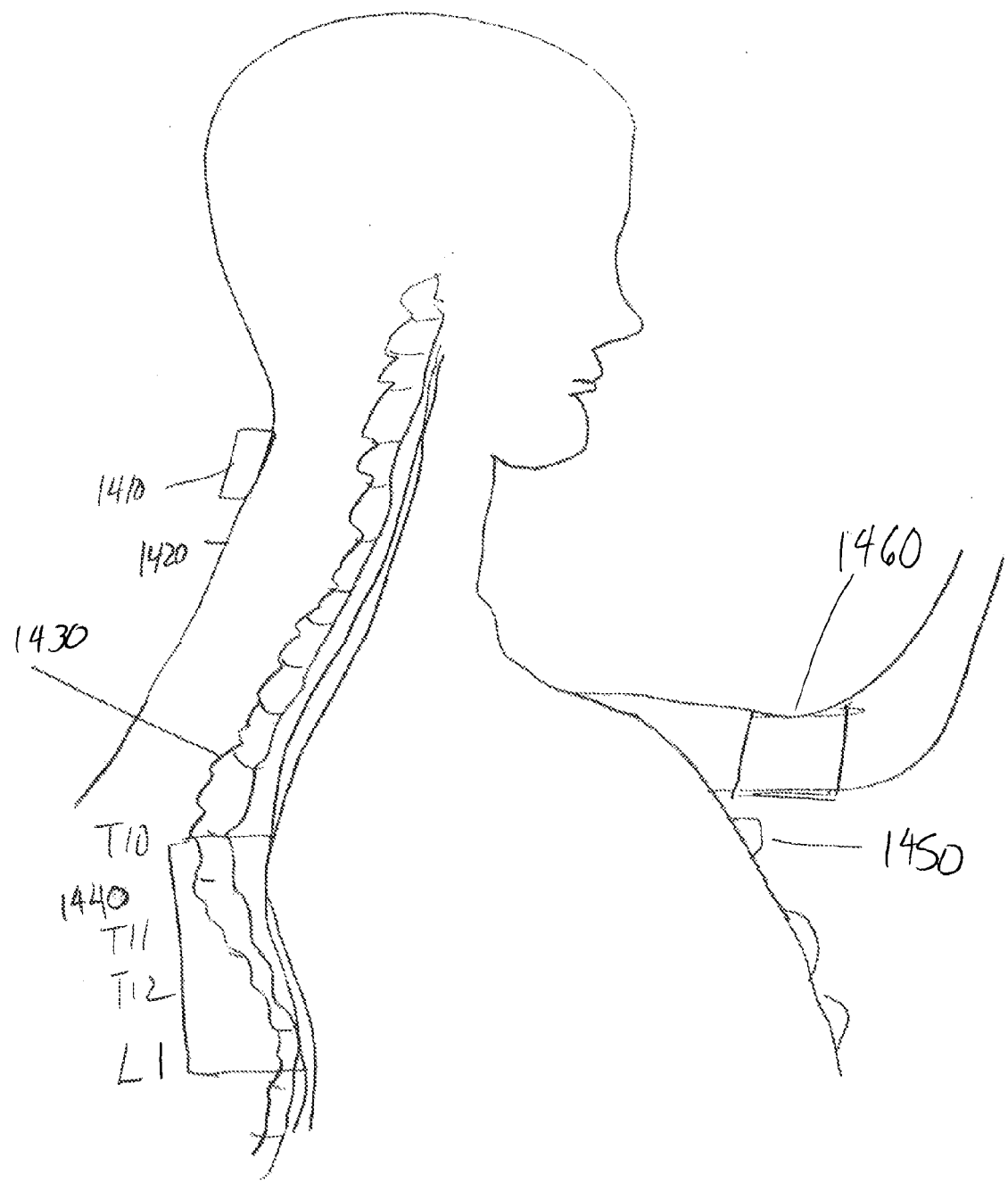
FIG. 14 illustrates an example placement of external stimulation devices and a system for treating anemia according to certain embodiments.
Figure 16:
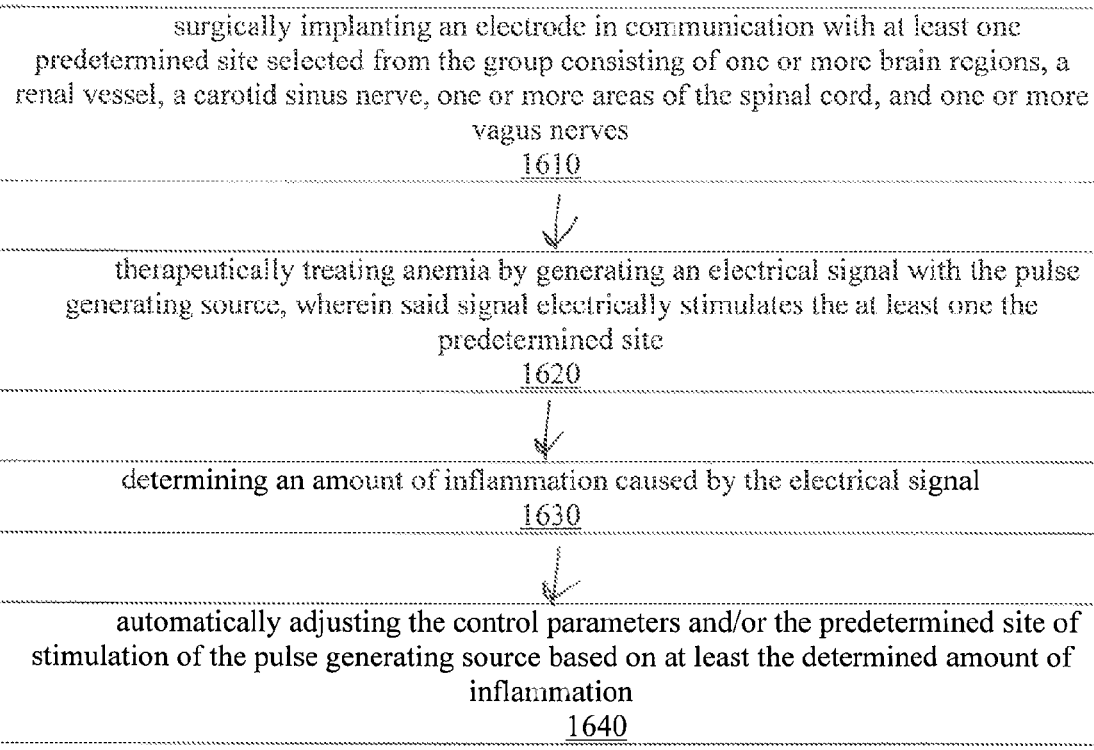
FIG. 16 illustrates an example method according to certain embodiments.

Transcutaneous Electrical Nerve Stimulation (TENS) and transcutaneous spinal electroanalgesia (TSE) devices have been used to manage pain in cancer patients (palliative treatment). An external stimulation device is similarly used on an acute basis to treat anemia in, for example, cancer patients, according to certain embodiments of the claimed invention. FIG. 14 illustrates an external neuromodulation system 1410.

As illustrated, a transcutaneous electrical nerve stimulation device 1410 is used to stimulate nerves of the neck 1420 involved in renal blood flow regulation and/or the inflammatory reflex. According to certain embodiments, a transcutaneous electrical nerve stimulation device is used to stimulate the right and/or carotid sinus nerve also known as the Hering's nerve), which is a branch of the ninth cranial nerves (CN IX), also known as the glossopharyngeal nerve (GPN). The right and left CSN include afferent fibers that convey information to the brain. The central nervous system may then trigger stimulation of the efferent nerves of the kidneys, and effect renal blood flow. Stimulation in the cervical region may also affect chemosensing activities of a carotid body, which can increase catecholamine production through communication with the central nervous system.

U.S. Publication No. 2013/0131753 ("Simon"), U.S. Pat. Nos. 4,702,254, 4,867,164 5,025,807, and 5,540,734, the disclosures of which are incorporated herein by reference in their entirety, provide appropriate techniques and devices amenable to transdermally stimulates of autonomic nerves in the area of the neck using electrical and/or magnetic stimulation, in accordance with certain embodiments of the claimed invention. As disclosed in Simon, a time-varying magnetic field, originating and confined to the outside of a patient, generates an electromagnetic field and/or induces eddy currents within the tissue of the patient. Magnetic stimulation is non-invasive because the magnetic field is produced by passing a time-varying current through a coil positioned outside the body. An electric field is induced at a distance causing electric current to flow within electrically conducting bodily tissue. U.S. Patent Publication Nos. US2005/0075701 and US2005/0075702, the disclosures of which are incorporated herein by reference in their entirety, describe pulse generators that may be used in an embodiment.

U.S. Publication No. US2005/0216062 ("Herbst"), the disclosures of which are incorporated herein by reference in their entirety, discloses a system for stimulating, blocking and/or modulating impulse to the electrodes or coils used non-invasively to stimulate deep nerves, used in certain embodiments. Herbst discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables.

Alternatively, or in addition, nerves of the spinal cord 1430 involved in renal blood flow regulation may be stimulated transcutaneously. Specifically, nerves in the T10-L1 region 1440 of the patient's spine may be stimulated. Generally, sympathetic innervation of the kidneys comes from the 10th through 12th thoracic spinal nerves, but can arise from as high as T6 and as low as L2, especially on the patient's right side. In certain embodiments, nerves in the T2-L2 region are stimulated.

U.S. Publication Nos, 2010/0152817 and 2012/0022612, the disclosure of each is incorporated herein by reference in its entirety, provide appropriate techniques and devices amenable to transdermally stimulates of autonomic nerves in the area of the spinal cord that can be used in accordance with certain embodiments to treat anemia in accordance with certain embodiments of the claimed invention.

A pre-pulse may be used in order to prepare the $Na^+$ channels of neurons in the spinal cord for activation in order to recruit more neurons.

As illustrated in FIG. 14, the external system may also include a surface EKG monitor 1450 and an external blood pressure monitor 1460, such as a blood pressure cuff, for use in a closed-loop system for determining the effect of the therapy, as described in further detail herein. Heart rate and heart rate variability may be monitored via the EKG and contractility can be monitored via arterial pressure sensors (e.g., the time derivative of the pressure can provide a good measure of contractility).

Renal Denervation

Methods of renal denervation are well known in the art. *Safety and efficacy of a novel multi-electrode renal denervation catheter in resistant hypertension: 3 month data from the EnligHTN I trial*, Worthley S., Tsioufis C., Worthley M., Sinhal A., Chew D., Meredith I., Malaiapan Y., Papademetriou V., Journal of the American College of Cardiology 2012 60 SUPPL, 17 (B62), incorporated herein by reference in its entirety, describes a method of renal denervation using the EnligHTN™ catheter, describes a method wherein a renal artery CT angiography is performed at baseline and repeated at 6 months. Utilizing femoral artery access with an 8Fr RDC guiding sheath the EnligHTN catheter is introduced into the renal artery, and RF energy delivered sequentially for 90 seconds per electrode. The catheter is repositioned, rotated and denervation repeated. Both renal arteries may be treated. Laparoscopic renal denervation may be used as an alternative or in conjunction with catheter radiofrequency ablation in order to safely affect a more complete renal denervation. An example of such an approach is described in Valente, in *Laparoscopic Renal Denervation for Intractable ADPK-Related Pain*, Nephrol Dial Transplant 16:60 (2001), incorporated herein by reference in its entirety.

Methods of radiofrequency catheter ablation are described in U.S. Publication Nos. 2013/0218029, 2013/0085489, 2013/0245621, 2013/0090637, 2011/0118726, and 2011/0137298, each of which is incorporated herein by reference in its entirety. Complete renal denervation is not required to significantly lower blood pressure and central nervous system over activity. Typical use of radiofrequency ablation catheters does not result in complete renal denervation. As illustrated in the method described in FIG. 15, a radiofrequency catheter ablation device is used to ablate the renal nerves of a patient 1510. The lead may be taken out of the patient and replaced with a permanently implantable lead, or the RF ablation catheter can be modified to provide a lead that is permanently implantable into the patient after a renal denervation procedure 1520 and configured for neurostimulation. In an embodiment, electrodes 22 illustrated in FIG. 3A above used for RF ablation may also be used for neuromodulation (either stimulation or block) as well. In an embodiment, separate electrodes 22 may be used for ablation and neuromodulation in order to minimize damage caused to the renal vessel by maneuvering the device. The tip of the lead may be secured distal to the ablation site 1530 in order to neuromodulate the remaining unablated nerves to produce EPO in accordance with the disclosure herein. Such an embodiment may be especially appropriate in the event that radiofrequency catheter ablation is performed in conjunction with laparoscopic renal denervation, where the more of the renal nerves may be denervated.

In the event that renal denervation results in anemia, neuromodulation of the central nervous system can alternatively, or additionally, be used to reverse the anemia, as described herein. According to the method illustrated in FIG. 15, the carotid sinus nerves, afferent renal nerves of the spinal cord (by stimulating the spinal cord at T10-L1), and/or the brain in order to stimulate the remaining efferent renal nerves through central nervous system stimulation and/or to stimulate the production of catecholamines and neuropeptides 1540.

It should be appreciated that various modifications may be incorporated into the disclosed embodiments based on the teachings herein. For example, the structure and functionality taught herein may be incorporated into types of devices other than the specific types of devices described above. Also, different types of stimulation signals may be applied to the nervous system consistent with the teachings herein. In addition, neurostimulation signals may be applied to other locations consistent with the teachings herein. Furthermore, a determination to apply neurostimulation may be made based on anemic conditions that are indicated in other ways consistent with the teachings herein.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting stimulation system 10 into a person for electrical stimulation of the predetermined site.

It should be appreciated from the above that the various structures and functions described herein may be incorporated into a variety of apparatuses (e.g., a stimulation device, a lead, a monitoring device, etc.) and implemented in a variety of ways. Different embodiments of such an apparatus may include a variety of hardware and software processing components. In certain embodiments, hardware components such as processors, controllers, state machines, logic, or some combination of these components, may be used to implement the described components or circuits.

In certain embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In certain embodiments some of the connections or couplings represented by the lead lines in the drawings may be in an integrated circuit, on a circuit board or implemented as discrete wires or in other ways.

The signals discussed herein may take various forms. For example, in certain embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in certain embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above it will be understood that the teachings herein are intended to cover any changes, adaptations or modifications which are within the scope of the disclosure as defined by any claims associated herewith.

What is claimed is:

1. A method of treating anemia in a human patient, the method comprising:
monitoring a hemoglobin level of the patient on a periodic basis;
determining an anemic condition based on the hemoglobin level;
determining one or more characteristics of the anemic condition;
selecting electrical stimulation parameters of a neurostimulation device based on the one or more characteristics of the anemic condition;
generating one or more stimulation signals to stimulate the patient's nervous system using the selected electrical stimulation parameters;
monitoring at least one of an autonomic balance or an inflammatory state of the patient resulting from the neurostimulation using the selected electrical stimulation parameters;
monitoring the patient's cardiac activity resulting from the neurostimulation using the selected electrical stimulation parameters; and
adapting the stimulation parameters of the neurostimulation device based on at least the patient's cardiac activity.

2. The method of claim 1 further comprising determining whether to provide stimulation of parasympathetic innervation, sympathetic innervation, or a combination of the two based on the anemic condition of the patient.

3. The method of claim 1, further comprising:
monitoring changes in at least one of: a severity of the anemic condition, a patient's heart rate, a quantity or severity of observed PVCs, or cardiac integrity; and
modifying stimulation parameters of the neurostimulation device if there is a change in at least one of: a severity of the anemic condition, the patient's heart rate, a quantity or severity of observed PVCs, or a cardiac integrity.

4. The method of claim 1, wherein determining an anemic condition based on the hemoglobin level comprises determining the patient's EPO observed/predicted (O/P) ratio.

5. The method of claim 1, wherein determining an anemic condition based on the hemoglobin level comprises determining the patient's EPO observed/predicted O/P ratio, transferrin saturation, and ferritin level.

6. A method of treating anemia in a human patient, the method comprising:

surgically implanting a pulse generating source comprising an electrode in communication with at least one predetermined site selected from the group consisting of one or more brain regions, a renal vessel, a carotid sinus nerve, one or more areas of the spinal cord, and one or more vagus nerves;

therapeutically treating anemia by generating an electrical signal with the pulse generating source, wherein said signal electrically stimulates the at least one predetermined site;

determining an amount of inflammation caused by the electrical signal; and automatically adjusting at least one of: one or more control parameters of the pulse generating source or the predetermined site of stimulation of the pulse generating source, based on at least the determined amount of inflammation.

7. The method of claim 6, wherein the at least one predetermined site comprises a NF-κB pathway of the patient's hypothalamus, and wherein the electrical signal blocks the NF-κB pathway of the patient's hypothalamus.

8. The method of claim 6, wherein the at least one predetermined site comprises at least one: an area of the patient's spinal cord at T10-L2, the patient's renal artery, the patient's paraventricular nucleus of the hypothalamus, the patient's cervical vagus nerve, or a NF-κB pathway of the hypothalamus of the patient.

9. A method of treating anemia in a human patient, the method comprising:

monitoring a hemoglobin level of the patient on a periodic basis;

determining an anemic condition based on the hemoglobin level, wherein determining an anemic condition based on the hemoglobin level comprises determining the patient's EPO observed/predicted O/P ratio, transferrin saturation, and ferritin level;

determining one or more characteristics of the anemic condition;

selecting electrical stimulation parameters of a neurostimulation device based on the one or more characteristics of the anemic condition;

generating one or more stimulation signals to stimulate the patient's nervous system using the selected electrical stimulation parameters;

monitoring at least one of an autonomic balance or an inflammatory state of the patient resulting from the neurostimulation using the selected electrical stimulation parameters.

10. The method of claim 9 further comprising determining whether to provide stimulation of parasympathetic innervation, sympathetic innervation, or a combination of the two based on the anemic condition of the patient.

11. The method of claim 9, further comprising:

monitoring changes in at least one of: a severity of the anemic condition, a patient's heart rate, a quantity or severity of observed PVCs, or cardiac integrity; and modifying stimulation parameters of the neurostimulation device if there is a change in at least one of: a severity of the anemic condition, the patient's heart rate, a quantity or severity of observed PVCs, or a cardiac integrity.

* * * * *